United States Patent
Barbera-Guillem

(10) Patent No.: US 6,224,866 B1
(45) Date of Patent: May 1, 2001

(54) IMMUNOTHERAPY OF B CELL INVOLVEMENT IN PROGRESSION OF SOLID, NONLYMPHOID TUMORS

(75) Inventor: Emilio Barbera-Guillem, Powell, OH (US)

(73) Assignee: BioCrystal Ltd., Westerville, OH (US)

( * ) Notice: Subject to any disclaimer, the term of this patent is extended or adjusted under 35 U.S.C. 154(b) by 0 days.

(21) Appl. No.: 09/411,116

(22) Filed: Oct. 4, 1999

Related U.S. Application Data

(60) Provisional application No. 60/103,350, filed on Oct. 7, 1998, and provisional application No. 60/117,526, filed on Jan. 28, 1999.

(51) Int. Cl.$^7$ .................. A61K 39/395; A61K 39/40; A61K 39/42
(52) U.S. Cl. .................... 424/130.1; 424/134.1; 424/138.1; 424/141.1; 424/143.1; 424/152.1; 424/153.1; 424/155.1
(58) Field of Search ............... 424/130.1, 134.1, 424/138.1, 141.1, 143.1, 152.1, 153.1, 155.1

(56) References Cited

U.S. PATENT DOCUMENTS

| | | |
|---|---|---|
| 5,593,676 | 1/1997 | Bhat et al. . |
| 5,736,137 | 4/1998 | Anderson et al. . |
| 5,776,456 | 7/1998 | Anderson et al. . |
| 5,789,554 | 8/1998 | Leung et al. . |
| 5,843,439 | 12/1998 | Anderson et al. . |

OTHER PUBLICATIONS

Seaver, Monoclonal Antibodies in Industry: More Difficult Than Originally Thought, Genetic Engineering News, vol. 14(14), pp. 10 and 21, Aug. 1994.*

Goodman and Gilman, The Pharmacological Basis of Theraputics, pp. 1202–1208 and 1457, 1990.*

Manson, Does antibody–dependent epitope masking permit progressive tumor growth in the face of cell mediated toxicity?, Immunology Today, vol. 12(10), pp. 352–355, Aug. 1994.*

* cited by examiner

Primary Examiner—Yvonne Eyler
Assistant Examiner—Jennifer Nichols
(74) Attorney, Agent, or Firm—M. Bud Nelson

(57) ABSTRACT

A method for treating a pro-tumor immune response in an individual having, or suspected of having, a pro-tumor immune response, by administering a therapeutically effective amount of an immunotherapeutic composition which binds to a determinant on B cells, resulting in B cell depletion including of B cells that may be involved in promotion of tumor progression. Also provided are immunotherapeutic compositions which can be used for treating a pro-tumor immune response.

46 Claims, 8 Drawing Sheets

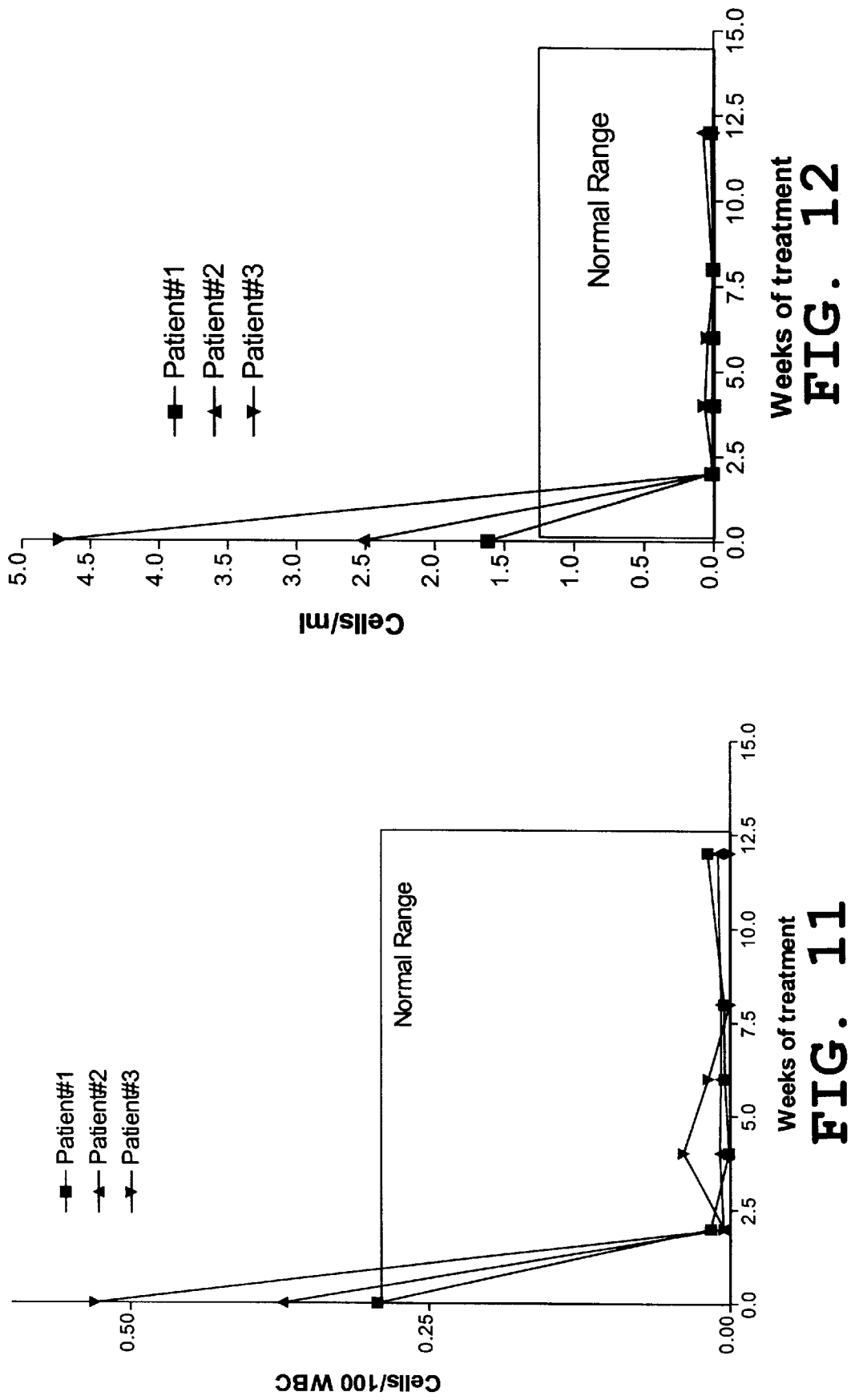

IMMUNOTHERAPY OF B CELL INVOLVEMENT IN PROGRESSION OF SOLID, NONLYMPHOID TUMORS

This is a nonprovisional application based on earlier co-pending provisional applications Ser. Nos. 60/103,350 filed Oct. 7, 1998 and 60/117,526, filed Jan. 28, 1999 which are herein substantially incorporated by reference.

FIELD OF THE INVENTION

The present invention is related to novel methods for immunotherapy of a pro-tumor immune response, whether present alone or present together with solid, non-lymphoid tumor, in humans. More particularly, the present invention is related to the methods for therapeutically treating B cells which may be involved in promotion of growth and metastasis of solid, nonlymphoid tumors.

BACKGROUND OF THE INVENTION

The response of an individual to tumor cells involves the reactions and counteractions mediated by both cellular and humoral arms of the immune system. Tumor cell growth may represent a disturbance in the equilibrium of the immune system that is pre-existing, and/or induced by the tumor cells themselves. However, most investigations to date have focused on the role of T cells in tumor immunity. The role of B cells in a tumor-bearing individual still remains unclear.

Previous studies have shown that lymph nodes regional to a primary tumor in cancer patients, and in in vivo experimental animal models of tumor development, can undergo a prominent expansion in the germinal centers (Eremin et al., 1980, *Br. J. Cancer* 41:62; Bertschmann et al., 1984, *Br. J. Cancer* 49:477–484). In these "involved" lymph nodes, there is often an increased number of immune cells that include B lymphocytes (B cells). However, the reason(s) for this observed B cell proliferative response remains unclear, and may be due to either activation and stimulation directly by tumor cells or tumor cell components, and/or indirectly by stimulation of T-helper cells which then activate and stimulate B cells. A recent study confirmed the increase in the number of B cells in lymph nodes regional to primary tumors (Ito et al., 1996, *Immunobiol.* 195:1–15). The number of B cells increase in the regional lymph nodes concomitantly with tumor development, and such B cells appear to be able to elicit anti-tumor immunity. In that regard, there are numerous reports that cancer patients have circulating antitumor antibodies (see, e.g., Carey et al., 1976, *Proc. Natl. Acad. Sci. USA* 73:3278–3282; Abe et al., 1989, *Cancer Res.* 80:271–276; Christensen et al., 1989, *Int. J. Cancer* 37:683–688). Thus, there appears that a humoral immune response towards tumor-associated antigens can be mounted in cancer patients. However, the role of the B cells in the host response to tumor, and the tumor associated antigens recognized by B cells, remain poorly defined.

Surgical removal of a primary tumor alone, thereby reducing the major portion of the tumor burden, is often inadequate to control regrowth or metastasis of the tumor; and hence often fails to significantly affect survival of a cancer patient. For example, of the more than 150,000 Americans who will develop colorectal carcinoma each year, it is estimated that 17% to 55% of them will develop or already have metastases in the liver (Zaveidsky et al., 1994, *Am. Surgeon* 60:929–933). Surgery, when possible, is used as a standard therapy for patients with isolated metastases (e.g., hepatic and/or pulmonary). After resection, the projected five year survival rate may range from 25–35%, the mean survival is about 31 months, and the 30-day mortality rate is about 4% (Wade, 1996, *J. Am. Coll. Surg.* 182:353–361). However, about 25% to 45% of patients who have had resection of their colorectal cancer later develop recurrences (Zaveidsky et al., 1994, supra). While new chemotherapeutics are being developed and tested for efficacy, many of the currently available cancer treatments are relatively ineffective. It has been reported that chemotherapy results in a durable response in only 4% of treated patients, and substantially prolongs the life of only an additional 3% of patients with advanced cancer (Smith et al., 1993, *J. Natl. Cancer Inst.* 85:1460–1474). Current treatments for metastases are both cost-prohibitive, relatively ineffective, and present with major toxicity. Regarding the latter and depending on the drug or drug combination used, systemic chemotherapy may result in one or more toxicities including hematologic, vascular, neural, gastro intestinal, renal, pulmonary, otologic, and lethal.

In contrast to solid, nonlymphoid tumors, there are numerous approaches and successes in treating B cell lymphoma (cancer cells of B cell origin). Such treatments include administration of immunologically active anti-CD20 antibodies to B cell lymphoma patients (see, e.g., U.S. Pat. No. 5,776,456); administration of an immunoconjugate comprising mAb Lym-1 coupled to ricin toxin A chain (see, e.g., U.S. Pat. No. 4,724,213); administration of an immunoconjugate comprising mAb LL2 (anti-CD22) coupled to chemotherapeutic agent (see, e.g., U.S. Pat. No. 5,789,554); and administration of an mAb alone, or an immunoconjugate comprising anti-CD19 mAb coupled to a chemotherapeutic agent (see, e.g., Hekman et al., 1991, *Cancer Immunol. Immunother.* 32:364–372; *Cancer Research Weekly*, Jun. 20, 1994, p.21; *Cancer Research Weekly*, Apr. 15, 1991, p.26).

We have discovered that certain soluble tumor antigens, shed from tumor cells of solid, nonlymphoid tumors, are capable of inducing an immune response which promotes tumor progression (comprising one or more of tumor growth, invasion, and metastasis). This mechanism of promotion of tumor progression involves the specific type of immune response induced by certain classes of shed tumor antigen, as described in more detail herein. This specific immune response, a "pro-tumor immune response", comprises (a) the contact or presence of shed tumor antigen in relation to the cell surface of B cells; (b) activation of such B cells to proliferate; (c) differentiation of B cells into plasma cells which secrete antibody against shed tumor antigen ("anti-shed tumor antigen antibody") which can interact with shed antigen in forming immune complexes; and (d) such immune complexes can act indirectly via immune effector cells, and/or directly on the nonlymphoid tumor cells, to mediate tumor progression.

Therefore, a need exists for methods which may be used to therapeutically treat a pro-tumor immune response, by treating B cells, in an individual; particularly in an individual who has a solid, nonlymphoid tumor, or an individual who is at high risk (e.g., environmentally and/or genetically) for developing a solid, nonlymphoid tumor, or an individual who has been treated for a solid, nonlymphoid tumor and thereby inherently carries a risk of recurrence of such tumor.

SUMMARY OF THE INVENTION

Accordingly, it is a primary object of the present invention to provide methods for treating a pro-tumor immune response by depleting B cells to inhibit the growth of primary solid, nonlymphoid tumors and/or their metastases.

It is another object of the present invention to provide methods for treating a pro-tumor immune response, wherein the treatment is directed to an individual's immune cells, wherein the immune cells are B cells, one or more subpopulations of which are involved in a pro-tumor immune response that can promote tumor progression of a solid, nonlymphoid tumor and/or its metastases.

It is a further object of the present invention to provide methods for treating an individual for (e.g., to inhibit, reduce, or eliminate) a pro-tumor immune response by directing the treatment to B cells, including one or more subpopulations of B lymphocytes, which may be found (a) in lymphoid tissue regional or distal to the site of a solid, nonlymphoid tumor; (b) infiltrating solid, nonlymphoid tumor; (c) circulating in body fluids such as peripheral blood; or (d) a combination thereof.

It is a further object of the present invention to provide methods for site-directed treatment of a pro-tumor immune response, wherein the treatment is directed to B cells which may include one or more subpopulations of B cells involved in a pro-tumor immune response, and wherein the immunotherapeutic composition is delivered in a relatively direct fashion to a localized region or tissue so as to better concentrate the immunotherapeutic composition in the proximity of targeted B cells.

It is also a further object of the present invention to provide methods for treating a pro-tumor immune response as an adjuvant regime in an individual who has indications of a pro-tumor immune response (e.g., altered B cell phenotype), who is in apparent remission of a solid, nonlymphoid tumor, and who is also at risk for recurrence of nonlymphoid tumor.

The foregoing objects are based on a discovery of a novel mechanism in which shed tumor antigen secreted by a solid, nonlymphoid tumor induces (activates) a subpopulation of B cells, in a pro-tumor immune response, to proliferate and differentiate into plasma cells which secrete anti-shed tumor antigen antibody that, when in immune complex form, can promote tumor progression of the primary tumor and of subsequent metastases. The objects of the invention are also achieved by providing methods for depleting B cells, one or more subpopulations of which may be involved in a pro-tumor immune response; and in a preferred embodiment, treatment is particularly directed to localized sites containing shed tumor antigen-specific B cells. In one embodiment, administered to an individual is a therapeutically effective amount of one or more immunotherapeutic compositions to deplete B cells present in a tissue selected from the group consisting of lymphoid tissues (e.g., either regional and/or distal relative to the site(s) of solid, nonlymphoid tumor), solid, nonlymphoid tumor, body fluids such as peripheral blood, or a combination thereof. In another embodiment, administered to an individual is a therapeutically effective amount of one or more anticancer agents (e.g., one or more chemotheraputic agents, one or more anti-inflammatory agents), in combination or conjunction with one or more immunotherapeutic compositions to treat B cells present in a tissue selected from the group consisting of lymphoid tissues, solid, nonlymphoid tumor, body fluids such as peripheral blood, or a combination thereof. In these embodiments, the function of an immunotherapeutic composition of the present invention is to cause B cell depletion, wherein B cell depletion may include one or more of: blocking of B cell function; functional inactivation of B cells; cytolysis of B cells; inhibiting the proliferation of B cells, including, but not limited to, one or more subpopulations of B cells involved pro-tumor immune response; reducing the amount of anti-shed tumor antigen antibody by depleting the number of B cells activated by shed tumor antigen ("shed tumor antigen-specific B cells"); and causing inactivation or cytolysis of B cells which have been primed or activated by shed tumor antigen. The immunotherapeutic compositions contact and bind to one or more determinants on B cells and may result in (e.g., cause, enable, or induce) B cell depletion, thereby immunomodulating the immune system to inhibit the tumor-promoting function of B cells involved in a pro-tumor immune response. Inhibiting the tumor-promoting function of B cells involved in a pro-tumor immune response may also inhibit one or more of the growth of the primary tumor, its ability to invade and/or metastasize, and growth of metastases.

The above and other objects, features, and advantages of the present invention will be apparent in the following Detailed Description of the Invention when read in conjunction with the accompanying drawings.

BRIEF DESCRIPTION OF THE DRAWINGS

FIG. 11 is a graph showing the depletion of CD19+ CD21+ sTn+ B cells effected by treatment of individuals with an immunotherapeutic composition.

FIG. 12 is a graph showing the depletion of CD19+ CD21+ B cells effected by treatment of individuals with an immunotherapeutic composition.

DETAILED DESCRIPTION OF THE PREFERRED EMBODIMENTS

Definitions

Figure 1:
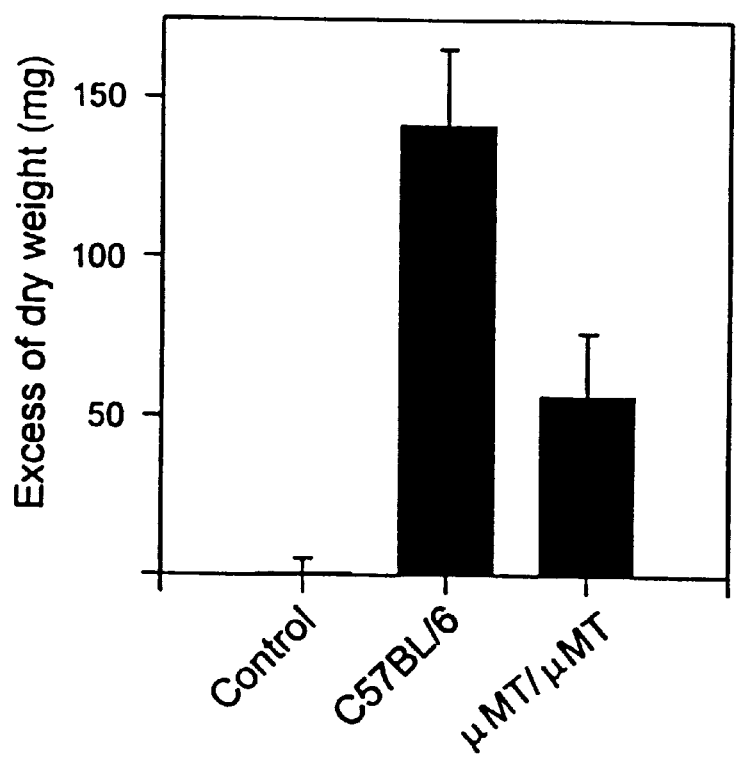
FIG. 1 is a bar graph illustrating a comparison between subcutaneous tumor growth in mice having an absence of functional B cells (C57B/μMT/μMT mice) as compared to B cell competent (C57BL/6) mice.

The term "depletion" is used herein in reference to B cells, and for purposes of the specification and claims, to mean one or more of: blocking of B cell function; functional inactivation of B cells; cytolysis of B cells; inhibiting the proliferation of B cells; inhibiting the differentiation of B cells to plasma cells; causing a B cell dysfunction which results in a therapeutic benefit to the treated individual; inhibiting the ability of shed tumor antigen-specific B cells to contribute to a pro-tumor immune response; reducing production of anti-shed tumor antigen antibody by inhibiting the activation of naive B cells by shed tumor antigen; inactivating B cells which have been primed or activated by shed tumor antigen; blocking of one or more functions of B cells which have been primed or activated by shed tumor antigen, wherein the one or more functions contribute indirectly or directly to a pro-tumor immune response; cytolysis of B cells which have been primed or activated by shed tumor antigen; and reducing the number of B cells which have been primed or activated by shed tumor antigen. B cell depletion may be a result of one or more mechanisms including, but not limited to, clonal inactivation, apoptosis, antibody-dependent cellular cytotoxicity, complement-mediated cytotoxicity, and a signal pathway mediated inactivation, dysfunction, or cell death.

The term "immunotherapeutic composition" is used herein, for purposes of the specification and claims, to mean a therapeutically effective amount of a composition (a) comprised of at least one affinity ligand which selectively (preferentially) binds to at least one determinant present on B cells, wherein the B cell preferentially comprise one or more subpopulations that comprise mature B cells, memory B cells, B cells of altered phenotype, and a combination thereof; and (b) whereupon upon contact and binding to such B cells, directly or indirectly results in (causes and/or enables) B cell depletion, including shed tumor antigen-specific B cells, and in sites that are foci of a pro-tumor immune response. Treatment with a therapeutically effective amount of the immunotherapeutic composition may result in a beneficial function. Such a beneficial function may include, but is not limited to, one or more of: inhibiting the proliferation of B cells which may be involved, or may be recruited to be involved, in a pro-tumor immune response; inhibiting proliferation of shed tumor antigen-specific B cells, and inhibiting differentiation of shed tumor antigen-specific B cells to plasma cells; and depleting B cells which have been primed or activated by shed tumor antigen. As an illustrative but non-limiting example, an anti-CD20 mAb, or an anti-Lym-1 mAb, or an anti-CD19 mAb, may selectively bind to B cells (via CD20, Lym-1, and CD19, respectively) and facilitate or result in B cell depletion. A bi-specific antibody mAb, anti CD3–CD19 mAb, may bind to T cells (via CD3) and B cells (CD19) to mediate T cell-B cell interactions that may facilitate B cell depletion.

Thus, in one embodiment, the present invention provides for the use of an immunotherapeutic composition in the manufacture of a pharmaceutical composition for use in a procedure for treating nonmalignant B cell involvement in a pro-tumor immune response; wherein the immunotherapeutic composition selectively contacts and binds to at least one determinant present on B cells (and in a preferred embodiment, the B cells comprise mature B cells, memory B cells, B cells of altered phenotype, and a combination thereof); wherein upon contact and binding to such B cells, the immunotherapeutic composition induces or causes B cell depletion; and wherein the procedure comprises administering to an individual a therapeutically effective amount of the pharmaceutical composition comprising the immunotherapeutic composition. Administering the immunotherapeutic composition to an individual may be by a mode which includes, but is not limited to, introducing the immunotherapeutic composition into a vascular access of the individual's tissue or organ to be treated, introducing the immunotherapeutic composition into peripheral blood, and a combination thereof.

The immunotherapeutic composition may further comprise an additional component comprising one or more of a chemotherapeutic agent, an anti-inflammatory agent, an anti-B cell agent, or a combination thereof. Chemotherapeutic agents are well known in the art (e.g., see the description to follow for "drugs" which include exemplary chemotherapeutic agents). Anti-inflammatory agents, well known in the art, may be used to suppress the inflammation which contributes to tumor progression as described herein. Illustrative but non-limiting examples of anti-inflammatory agents include non-steroidal anti-inflammatory drugs (e.g., aspirin, ibuprofen, naproxen, and the like), and COX-2 inhibitors (e.g., rofecoxib, and celecoxib). The invention may be practiced with a preferred additional component to the exclusion of other additional components. The "anti-B cell agent" is an agent that acts directly against B cells, or acts indirectly (e.g., stimulates a Th1 response, thereby diverting away from a Th2 response may enhance B cell involvement in a pro-tumor immune response); wherein the anti-B cell agent comprises an immunomodulatory agent, or cytolytic agent, or a vector capable of encoding in a B cell an immunomodulatory agent or cytolytic agent that is subsequently introduced into B cells. In one embodiment, the additional component is administered separately (e.g., non-conjugated to; whether administered simultaneously, or administered separately, as part of a treatment regimen) with respect to the immunotherapeutic composition. In another embodiment, the additional component may be coupled to the affinity ligand of the immunotherapeutic composition; wherein the affinity ligand serves to selectively bind the B cells, thereby bringing the additional component in contact with or in functional proximity of B cells that may be involved in a pro-tumor immune response that promotes tumor progression. An immunomodulatory agent is an agent which, by interacting directly with such B cells or with naive CD4+ cells or with follicular dendritic cells, inhibits or prevents one or more of the following: activation and/or proliferation of B cells induced by the shed tumor antigen (e.g., shed tumor antigen by itself, or as presented to B cells by antigen presenting cells); secretion by plasma cells of anti-shed tumor antigen antibody which, in immune complex form, promotes tumor progression; a Th2 response. Such immunomodulatory agents may include, but are not limited to, a therapeutically effective amount of: cytokines, biologically active peptides, immunostimulatory sequences, drugs, and a combination thereof. The invention may be practiced with a preferred immunomodulatory agent to the exclusion of other immunomodulatory agents. For example, soluble CD21 has been shown to reduce antibody responses by blocking CD21 ligand on follicular dendritic cells and/or by binding C3 fragments associated with immune complexes (Qin et al., 1998, *J. Immunol.* 161:4549–54). Also, IL-12 has been shown to be a potent inducer of naive CD4+ cells towards a Th1 response (Palm et al.,1996/1997 *Immunobiology* 196:475–484; Jeannin et al., 1996, *J. Immunol.* 156:315903165). Further, certain short bacterial immunostimulatory DNA sequences ("ISS", containing unmethylated CpG motifs), have been shown to be able to stimulate a Th1 response (e.g., by inducing IL-12 production), and hence stimulate a cell-mediated immune response (Roman et al., 1997, *Nat. Med.* 3:849–854; Lipford et al., 1997, *Eur. J. Immunol.* 27:3420–3426). A cytolytic agent is an agent that, by interacting directly with such B cells, causes B cell cytotoxicity. Such cytolytic agents may include, but are not limited to, a therapeutically effective amount of: toxins; drugs; enzymes; cytokines; radionuclides; photodynamic agents; and molecules which induce apoptosis (e.g., Fas ligand). Toxins may include a therapeutically effective amount of ricin A chain, mutant Pseudomonas exotoxins, diphtheria toxoid, streptonigrin, boamycin, saporin, gelonin, and pokeweed antiviral protein. Drugs may include a therapeutically effective amount of cytotoxic drugs including, but not limited to, fludarabine, chlorambucil, daunorubicin, doxorubicin (e.g., in liposomes), cisplatin, bleomycin, melphalan, mitomycin-C, and methotrexate. Due to the sensitivity of B cells to radiation, radionuclides may include, but are not limited to, radiometals such as yttrium which emits a high energy beta particle, and $I^{125}$ that emits Auger electrons, that may be absorbed by adjacent B cells. Photodynamic agents may include therapeutically effective amounts of porphyrins and their derivatives. The methods for coupling ligands or targeting molecules with therapeutic agents are well known to those skilled in the art (See, for example, conjugates as reviewed by Ghetie et al., 1994, *Pharmacol. Ther.* 63:209–34; U.S. Pat. No. 5,789,554, the disclosure of which is herein incorporated by reference). Often such methods utilize one of several available heterobifunctional reagents used for coupling or linking molecules.

Also, the immunotherapeutic composition may further comprise a pharmaceutically acceptable carrier medium for facilitating infusion into the bloodstream, or infusion into a vascular access (including lymphatics) of the individual's tissue to be treated. Such pharmaceutically acceptable carrier media are known to those skilled in the art to include buffered saline solutions, buffered carbohydrate solutions, liposomes (Phillips et al., 1994, *J. Immunother. Emphasis Tumor Immunol.* 15:185–93), sterile water, and the like.

The term "determinant" with reference to B cells, is used herein, for purposes of the specification and claims, to mean a molecule which is preferentially expressed by B cells, or one or more subpopulations thereof which include memory B cells, mature B cells, and B cells of altered phenotype (see, e.g., Table 3); wherein the molecule is involved in and responsible for selective binding to an affinity ligand having binding specificity and avidity for the determinant. Cell-associated determinants may include, but are not limited to, molecules, receptors, components, or surface immunoglobulin, present on the surface of the cell membrane. "Preferentially expressed" is used herein to mean that the cell-associated determinant is expressed on a substantial number (approximately 40% or greater) of the B cells, or of a subpopulation thereof, which are targeted by the immunotherapeutic composition. In a preferred embodiment, the determinant is primarily expressed on B cells, with little or no expression of the determinant (as relative to the number of cells expressing the determinant or to the level of expression as compared to B cells) by other subpopulations of immune cells (with the possible exception of dendritic cells; e.g., CD21) contained within a region or tissue to which the immunotherapeutic agent is targeted or administered. In a preferred embodiment, the determinant is selected from the group consisting of CD19, CD20 (see, e.g., U.S. Pat. No. 5,776,456, the disclosure of which is herein incorporated by reference), CD21, CD22 (see, e.g., LL2, U.S. Pat. No. 5,789,554, the disclosure of which is herein incorporated by reference; Erickson et al., 1996, *Int. Immunol.* 8:1121–9), Lym-1 (see, e.g., U.S. Pat. No. 5,789,554, the disclosure of which is herein incorporated by reference), CDIM (see, e.g., U.S. Pat. No. 5,593,676, the disclosure of which is herein incorporated by reference), sIg having binding specificity for shed tumor antigen, and a combination thereof.

The term "B cells" is used herein, for purposes of the specification and claims, and particularly in reference to treating solid, non-lymphoid tumor and a pro-tumor immune response or the presence of a pro-tumor immune response without clinically evident tumor comprising depleting B cells described herein, to mean mammalian (and preferably human) nonmalignant B cells. As known to those skilled in the art, malignant B cells refers to cancer cells of B cell origin, such as B cell lymphomas, and B cell leukemias. Thus, the term "B cells", as used herein in reference to depleting B cells and in treating a pro-tumor immune response, specifically excludes B cell lymphomas, B cell leukemias, and cancer cells of B cell origin. In that regard, nonmalignant B cells comprise one or more of: memory B cells; mature B cells; a subpopulation thereof (e.g., B cells which have a cell surface-bound immunoglobulin comprising antibody against shed tumor antigen; or B cells of altered phenotype-see Table 3); and a combination thereof. The one or more subpopulations of B cells may be involved in (including may contribute to) one or more of a pro-tumor immune response, and promotion of tumor progression, as will be more apparent from the following embodiments.

The term "lymphoid tissue" is used herein, for purposes of the specification and claims, to mean a tissue which contains localized areas (e.g., follicles) of antigen presenting cells and B cells, and in which can be induced an immune response involving B cells. Such lymphoid tissues comprise lymph nodes; milky patches in the mesenterium of the intestine; omentum; appendix; Peyer's patches; loose connective tissue (e.g., associated with vessels in the walls of the aorta); lymphatic vessels; submucosal spaces; subserosa spaces; peritoneal cavity; ligaments (e.g., gastro-hepatic ligament); artherosclerotic plaques containing trapped B cells; and epineura.

The term "metastases" is used herein, for purposes of the specification and claims, to mean metastatic cells from a primary tumor wherein the primary tumor is a solid, non-lymphoid tumor, as will be more apparent from the following embodiments.

The term "affinity ligand" is used herein, for purposes of the specification and claims, to mean a molecule which has binding specificity and avidity for a determinant associated with B cells that may be present in lymphoid tissues, and/or infiltrating solid, nonlymphoid tumors, and/or circulating in body fluids such as peripheral blood. In general, affinity ligands are known to those skilled in the art to include, but are not limited to, lectins (or fragments or derivatives thereof which retain specific binding activity), monoclonal antibodies ("mAb", including chimeric or genetically modified monoclonal antibodies which may be preferable for administration to humans), peptides, and aptamers. The term "monoclonal antibody" is also used herein, for purposes of the specification and claims, to include immunoreactive fragments or immunoreactive derivatives (e.g., peptides) derived from a mAb molecule, which retain all or a portion of the binding function of the whole mAb molecule. Such immunoreactive fragments or immunoreactive derivatives are known to those skilled in the art to include F(ab')$_2$, Fab', Fab, Fv, scFV, Fd', Fd, and the like. Methods for producing the various fragments from mAbs are well known in the art (see, e.g., Plückthum, 1992, Immunol. Rev. 130:152–188). For example, F(ab')$_2$ can be produced by pepsin digestion of the monoclonal antibody, and Fab' may be produced by reducing the disulfide bridges of F(ab')$_2$ fragments. Fab fragments can be produced by papain digestion of the monoclonal antibody, whereas Fv can be prepared according to methods described in U.S. Pat. No. 4,642,334. Single chain derivatives can be produced as described in U.S. Pat. No. 4,946,778. The construction of chimeric antibodies is now a straightforward procedure (Adair, 1992, Immunological Reviews 130: 5–40,) in which the chimeric antibody is made by joining the murine variable region to a human constant region. Additionally, "humanized" antibodies may be made by joining the hypervariable regions of the murine monoclonal antibody to a constant region and portions of variable region (light chain and heavy chain) sequences of human immunoglobulins using one of several techniques known in the art (Adair, 1992, supra; Singer et al., 1993, J. Immunol. 150:2844–2857). Methods for making a chimeric non-human/human mAb in general, and a chimeric anti-CD20 mAb in particular, are described in detail in U.S. Pat. No. 5,736,137. The chimeric anti-CD20 antibody described in U.S. Pat. No. 5,736,137 has been reported to be therapeutically active on its own; e.g., does not require coupling to a toxin or radioisotope to induce cytolysis of targeted B cells. Likewise, chimeric anti-CD22 antibody has been previously described in U.S. Pat. No. 5,789,554. Likewise, a cross-linking of a B cell by an anti-CDIM mAb has been reported to induce a cellular response ultimately resulting in cell death (U.S. Pat. No. 5,593,676). In a preferred embodiment, affinity ligands may include, but are not limited to, a mAb having binding specificity for one of CD19, CD20, CD21, CD22, CDIM, or Lym-1. Aptamers can be made against B cell determinants using methods described in U.S. Pat. No. 5,789,157 (the disclosure of which is herein incorporated by reference).

The term "solid, non-lymphoid tumor" is used herein, for purposes of the specification and claims, to mean any primary tumor of ductal epithelial cell origin, including, but not limited to, tumors originating in the liver, lung, brain, lymph node, bone marrow, breast, colon, pancreas, stomach, esophagus, gastrointestinal tract, or reproductive tract (cervix, ovaries, endometrium etc.); and which produces shed tumor antigen (e.g., serous, or endometroid, or mucinous tumors). As apparent to one skilled in the art, lymphoid tumors, including B cell lymphomas, and leukemias are excluded from the definition of solid, nonlymphoid tumors or their metastases. For the purposes of the present invention, "solid, non-lymphoid tumor" may additionally encompass melanoma which produces shed tumor antigen.

The term "organ" is used herein, for purposes of the specification and claims, to mean any tissues or organs in which solid, non-lymphoid tumors, or their metastases, may develop. Such organ may include, but is not limited to, breast, liver, lung, brain, lymph node, bone marrow, colon, stomach, pancreas, appendix, small bowel, esophagus, prostate, or reproductive organ.

The term "shed tumor antigen" is used herein, for purposes of the specification and claims, to mean a glycoprotein that:

(a) is released from a primary tumor or its metastases, thereby becoming soluble and allowing for movement into tissues;
(b) comprises a molecule having repeated carbohydrate chains which may present a terminal, repeated carbohydrate epitope;
(c) interacts with a B cell surface receptor in activating (by itself or in the presence of another B cell stimulatory factor, such as may be displayed by presenting antigen presenting cells) B cells to shed tumor antigen;
(d) induces a humoral immune response resulting in the production and secretion of anti-shed tumor antigen antibody; and
(e) can interact with anti-shed tumor antigen antibody in forming immune complexes, wherein the immune complexes may bind and cross-link FcγRI present on the surface of FcγRI expressing cells.

With regard to the tumor antigen being soluble, the tumor antigen is noncellular ("shed") tumor. Non-cellular tumor antigen comprises soluble tumor antigen that is not an integral part of a living tumor cell. Such shed tumor antigen exists in a form selected from the group consisting of free form (shed tumor antigen alone), in an immune complex form (shed tumor antigen bound to anti-shed tumor antigen antibody), in a form as presented on the surface of an antigen presenting cell (e.g., follicular dendritic cells), in a form as bound to the cell surface of B cells, and as a form in tumor cell membranes existing apart from living tumor cells (i.e., soluble membrane complexes representing portions of dead tumor cells).

With regard to the shed tumor antigen comprising repeated carbohydrate chains containing one or more epitopes (hence, repeated epitopes), that is glycoprotein in composition, and that can interact with anti-shed tumor antigen antibody in forming immune complexes, wherein the immune complexes may bind and cross-link FcγRI present on the surface of FcγRI expressing cells, and for purposes of illustration, and not limitation, exemplifying such shed tumor antigen are mucins and mucin-like molecules. For a review of the structure of the family of mucin molecules, see Finn et al. (1995, Immunol. Rev., 145:62–89). Briefly, mucins are high molecular weight glycoproteins (e.g., greater than about 100 kiloDaltons in molecular mass) of which a significant portion of the polypeptide backbone comprises a domain composed of a tandomly repeating peptide subunits (e.g. about 20 to about 125 repeats). Mucins are found on normal ductal epithelial cells in sequestered locations that are not normally exposed to the immune system (e.g., restricted to the lumen of duct). However, in processes such as transformation (e.g., pre-cancerous) or tumor development, and due to various factors (e.g., the increased production of mucin, lack of availability of glycosyltransferases), non-lymphoid tumor cells produce mucin in an underglycosylated (incompletely glycosylated) form and/or in a form of altered glycosylation (e.g., with a terminal sialic acid group). An immune response against tumor cell-produced mucin is thought to be primarily directed against one or more epitopes on the mucin glycoprotein which is exposed to the immune system as a result of underglycosylation or altered glycosylation. Thus, because of the underglycosylation or altered glycosylation in growing tumors, the shed tumor mucin has epitopes not normally found on mucin or not normally exposed to the immune system. Such epitopes may include, but are not limited to, carbohydrate epitopes comprising the sialyl Tn (sTn) antigen (substantially comprising the NeuAc portion of NeuAcα2→6GalNAcα1→O-Ser- or Thr); the Tn antigen (comprising the GalNAc portion of GalNAcα1→O-Ser- or Thr), the T antigen, and other sialic acid containing epitopes (e.g., substantially comprising NeuAcα2 on the carbohydrate chains (a) NeuAcα2→6Gal→O-Ser- or Thr, (b) NeuAcα2→3Gal→O-Ser- or (c) NeuAcα2→3GalNAc→O-Ser- or Thr). Examples of a mucin-like glycoprotein which is differentially glycosylated by tumor cells, and is shed by tumor cells, are SSEA-1 antigen and carcinoembryonic antigen (CEA).

Tumor-associated glycoproteins, and characterizations such as the nature of carbohydrate chain structure and/or monoclonal antibody binding, are known to those skilled in the art (see, e.g., Table V of Hakomori, 1989, *Adv. Cancer Res.* 52:257–331). Tumor-associated glycoproteins which are known to those skilled in the art as being found in a soluble form include, but are not limited, to the human equivalents of those presented in Table 1.

TABLE 1

| Soluble-tumor Ag | Antibody | Characteristic |
| --- | --- | --- |
| sialyl SSEA-1 ("SLX") | FH-6 | pancreatic, lung, gastric, ovarian, cervical adeno-carcinomas |
| PA8-15 | mAb PA8-15 | pancreatic, gastro-intestinal carcinoma |
| MUSE 11 | mAb MUSE 11 | adenocarcinoma, pancreatic cancer |
| Her-2/neu | mAb GFD-OA-p185-1 | 185 kD; various carcinomas |
| TA90 or U-TAA | mAb ADI-40F4 | melanoma |
| KL-6 antigen | mAb K1-6 | various adenocarcinomas |

For purposes of illustration, and not limitation, in a preferred embodiment of the present invention, the shed tumor antigen comprises one or more antigens on the gene product of the MUC-1 gene (also known as polymorphic epithelial mucin; hereinafter referred to as "mucin"). In a more preferred embodiment, the shed tumor antigen is mucin, and the terminal, repeated carbohydrate epitope to which anti-shed tumor antigen-antibody is directed comprises sTn antigen.

With regard to a humoral immune response that may be induced by the shed tumor antigen, it is known that the immune response induced by tumor cell-associated mucin is predominantly cellular (CD8+), with little or no antibody produced. In contrast to mucin bound to the surface of whole tumor cells, shed mucin induces a humoral immune response that eventually results in antibody production, but not cytotoxic T cell responses (Apostolopoulos et al., 1994, *Cancer Res.* 54:5186). However, it was not known that such an immune response can promote tumor progression. In the development of the present invention, the inventor determined that anti-shed tumor antigen antibody, particularly in the form of immune complexes also comprising shed tumor antigen, may promote tumor progression in a pro-tumor immune response; and further, may inhibit the development of an effective antitumor humoral immune response.

The term "individual" is used herein, for purposes of the specification and claims, to mean a mammal; and preferably a human. An individual who is at risk of developing, or has developed, a pro-tumor immune response may include an individual having a primary tumor comprising a solid, non-lymphoid tumor and/or its metastases; an individual having a pre-cancerous lesion comprising transformed (abnormal in proliferation and/or genetic makeup as compared to normal epithelial cells of the same type) cells of ductal epithelial origin which release shed tumor antigen; an individual who is at high risk (e.g., environmentally and/or genetically) for developing a solid, nonlymphoid tumor; or an individual who has been treated for a solid, non-lymphoid tumor and thereby inherently carries a risk of recurrence. In a preferred embodiment of the present invention, the method and compositions are intended for use to treat B cells localized in one or more body tissues (e.g., lymphoid tissue, solid, nonlymphoid tumor); body fluids such as peripheral blood, or a combination thereof in individuals at risk for developing, or who have developed, a pro-tumor immune response.

The term "vector" or "expression vector" is used herein for purposes of the specification and claims, to mean vectors used in accordance with the present invention as a vehicle for introducing into and expressing in a mammalian cell a desired gene. As known to those skilled in the art, such vectors can be selected from plasmids, viruses, and retroviruses. For a recent review of vectors useful in gene therapy of cancer, see Weichselbaum and Kufe (1997, *Lancet*, 349:S10–S12). The features of a vector which make it useful in the methods of the present invention include that it have a selection marker for identifying vector which has inserted therein a gene encoding an anti-B cell agent; restriction sites to facilitate cloning of a gene encoding an anti-B cell agent; and the ability of the vector to enter and/or replicate in mammalian cells. Examples of a preferred vector for the in vivo introduction of a recombinant vector into mammalian cells include, but are not limited to viral vectors. Virus-based vectors are one preferred vehicle as they infect cells in vivo, wherein during the infection process the viral genetic material is transferred into the cells. A retroviral vector, such as a plasmid containing AAV (Adeno-associated virus) sequences, has been described previously (see for example Chatterjee et al., 1992, *Science*, 258:1485–1488; U.S. Pat. No. 5,252,479, herein incorporated by reference). In one embodiment, the AAV vector contains inverted terminal repeats (ITR) with a selection marker such as the gene encoding neomycin resistance, an SV40 promoter, a polylinker, and other plasmid sequences. A promoter in the ITR drives the expression of the neomycin phosphotransferase gene, whereas the SV40 promoter drives expression of the operably linked gene encoding an anti-B cell agent to be expressed. The inverted terminal repeats of the AAV vector provide a means for integrating the vector, and sequences inserted therein, into the chromosome as the repeats serve as a sequence which has been shown to insert site-specifically, rather than randomly, into chromosomes. Examples of other vectors for the in vitro or in vivo introduction into mammalian cells include retroviral vectors (Miller et al., 1989, *BioTechniques* 7:980–990; Korman et al., 1987, *Proc. Natl. Acad. Sci. USA* 84:2150–54), papovavirus episomes (U.S. Pat. No. 5,624,820, herein incorporated by reference), and adenovirus vectors (U.S. Pat. No. 5,585,362, herein incorporated by reference). Such vectors can utilize tissue-specific promoters in targeting expression to B cells. For example, B cell-specific promoters are known to those skilled in the art to include, but are not limited to, immunoglobulin promoters (see, e.g., Thoger et al., 1997, *Mol. Immunol.* 34:97–107; Luo and Roeder, 1995, *Mol. Cell. Biol.* 15:4115–24; Cockerill and Klinken, 1990, *Mol. Cell. Biol.* 10:1293–6), class II transactivator promoter (Lennon et al., 1997, *Immunogenetics* 45:266–73), mb-1 promoter (Fitzsimmons et al., 1996, *Genes Dev.* 10:2198–211; Travis et al., 1991, *Mol. Cell. Biol.* 11:5756–66), human B29 gene promoter (Thompson et al., 1996, *Blood* 87:666–73; Omori and Wall, 1993, *Proc. Natl. Acad. Sci. USA* 90:11723–7), and Fc epsilon RII promoter (Dierks et al., 1994, *Mol. Immunol.* 31:1181–89).

The term "pro-tumor immune response", for purposes of the specification and claims, means a humoral immune response against a repeated, antigenic carbohydrate determinant of shed tumor antigen that results in immune complexes formed between antibody (particularly IgG) to shed tumor antigen, and shed tumor antigen. Such immune complexes may then promote tumor progression by one or more mechanisms comprising: binding and crosslinking Fc receptors (e.g., FcγRI) on immune effector cells resulting in the release of inflammatory mediators which promote angiogenesis for, and invasion by, tumor cells; binding and crosslinking FcγRI on FcγRI-expressing tumor cells resulting in an induction of tumor cell proliferation, and an increase in the amount of shed tumor antigen released by the tumor cells; and binding and crosslinking Fc receptors (e.g., FcγRI) on Fc receptor expressing endothelial cells resulting in an induction of endothelial cell proliferation and/or release of factors promoting angiogenesis. Immune effector cells are host cells which are mediators of inflammation and/or angiogenesis (e.g., one or more of granulocytes, macrophages, vascular endothelial cells) that are capable of inducing a cascade of processes which promote tumor progression.

The present invention relates to a discovery by the inventor that in a pro-tumor immune response, a significant (detectable) number of B cells comprising shed tumor antigen-specific B cells and B cells of altered phenotype may be found in tissues of an individual having a pro-tumor immune response. Such B cells may be retained locally in lymphoid tissues containing persisting deposits of shed tumor antigen, and/or may be circulating in body fluids such as peripheral blood, and/or may be infiltrating a tumor, if present. In a preferred embodiment, a pro-tumor immune response may comprise: contact of shed tumor antigen with B cells resulting in shed tumor antigen-specific B cells, and ultimately resulting in plasma cells secreting anti-shed tumor antigen antibody (in a preferred class as IgG)(hence, an example of B cell "involvement" in a pro-tumor immune response); lymphoid tissues containing follicular dendritic cells presenting shed tumor antigen, in the form of immune complexes, to B cells, and wherein such follicular dendritic cells may serve as a persisting source of antigen presentation; and immune complexes (containing shed tumor antigen complexed to anti-shed tumor antigen antibody) in sufficient amounts which may act to promote tumor progression. Such immune complexes may promote tumor progression by one or more mechanisms, such as: (a) acting as a chemoattractant in causing immune effector cells to migrate to localized deposits of such immune complexes; (b) by binding Fc receptors on granulocytes and macrophages which may then mediate release of tissue degrading enzymes which can degrade connective tissue matrix (facilitating invasion), and cytokines/growth factors which can promote angiogenesis, (c) by binding Fc receptors on tumor cells which induces tumor growth and/or an increase in production and secretion of shed tumor antigen, and (d) by binding to endothelial cells and causing angiogenesis and/or vasodilation.

According to one embodiment of a method according to the present invention for treating a pro-tumor immune response by depleting B cells that may be involved in progression of solid, non-lymphoid tumors, administered to an individual is a therapeutically effective amount of an immunotherapeutic composition. The immunotherapeutic composition may be administered by a mode which facilitates infusion into a vascular access of the individual's tissue or organ to be treated, thereby delivering the immunotherapeutic composition in a site-directed manner. A vascular access may comprise a blood vessel, lymphatic vessel, or a combination thereof, that serves the targeted tissue or organ. The tissue may comprise lymphoid tissue; solid, non-lymphoid tumor tissue, or a combination thereof; and the organ may comprise the organ in which such tissue is present. The immunotherapeutic composition may be administered by itself, or as part of a regimen of anticancer therapy (e.g. in conjunction with one or more chemotherapeutic agents, one or more anti-inflammatory agents, one or more anti-B cell agents, or a combination thereof).

In another embodiment of a method according to the present invention for treating a pro-tumor immune response by depleting B cells that may be involved in progression of solid, non-lymphoid tumors, administered to an individual is a therapeutically effective amount of an immunotherapeutic composition by a mode which facilitates infusion into peripheral blood (e.g., intravenously). The immunotherapeutic composition may be administered by itself, or as part of a regimen of anticancer therapy (e.g. in conjunction with one or more chemotherapeutic agents, one or more anti-inflammatory agents, one or more anti-B cell agents, or a combination thereof). In another embodiment, the method comprises administering a therapeutically effective amount of an immunotherapeutic composition which further comprises a therapeutically effective amount of an anti-B cell agent. The anti-B cell agent may act directly on the B cell or may be encoded by a vector which induces expression of the anti-B cell agent in an individual's B cells. The vector, in accordance with the present invention, is a vehicle for introducing into, and expressing in B cells a therapeutically effective amount of a gene encoding an anti-B cell agent. The affinity ligand facilitates selectively delivery of the vector to the targeted B cells.

In these illustrated embodiments, the immunotherapeutic composition may further comprises a pharmaceutically acceptable carrier. Such pharmaceutically acceptable carriers are known in the art to include, but are not limited to, physiological solutions, sterile water, liposomes, other delivery vehicles, and compositions which facilitate infection or introduction of the vector into B cells (e.g., such compositions may include, but are not limited to, microparticles which permit or enhance uptake or introduction of vector into the target cells).

For purposes of the description, the methods and compositions of the present invention will be illustrated in the following examples.

EXAMPLE 1

This, and the following embodiments, provide evidence of the B cell involvement, and the specific type of immune response related thereto, which promotes tumor progression and metastasis. In those embodiments illustrated in Examples 1–4 herein, it is important to consider the following concept. Various strains of mice were used as a standard animal model for evaluating whether a B cell response may be involved in promotion of tumor progression. In the tumor bearing mice of B cell competent strains, a similar proliferative germinal center B cell response was observed in lymph nodes regional to a primary tumor as observed in tumor bearing humans. In that regard, and to assess whether B cells are effector cells of, at least in part, a tumor promoting immune response, an in vivo standard experimental model comprising tumor bearing mice was used. One group of C57 μMT/μMT ("B cell deficient"; i.e., do not develop competent B cell system) mice was injected intrasplenically with $10^6$ B16F10 melanoma tumor cells. One group of C57BL/6 (immunocompetent) mice was injected intrasplenically with $10^6$ B16F10 tumor cells. One group of mice (control) received PBS only. Fourteen days postinjection, spleens from the three groups of mice were evaluated for tumor growth by measuring spleen weight. For spleen weight determinations, the spleens were removed; dried by immersion in 100% ethanol for seven days during which period the ethanol evaporated; and the dried spleens were weighed, and an average for the group reported. As shown in FIG. 1, the spleen weight was significantly decreased in B cell deficient (C57 $\mu$MT/$\mu$MT) mice, as compared to B cell-competent mice, indicative of a decreased ability of B cell deficient mice to mediate tumor progression.

Figure 2:
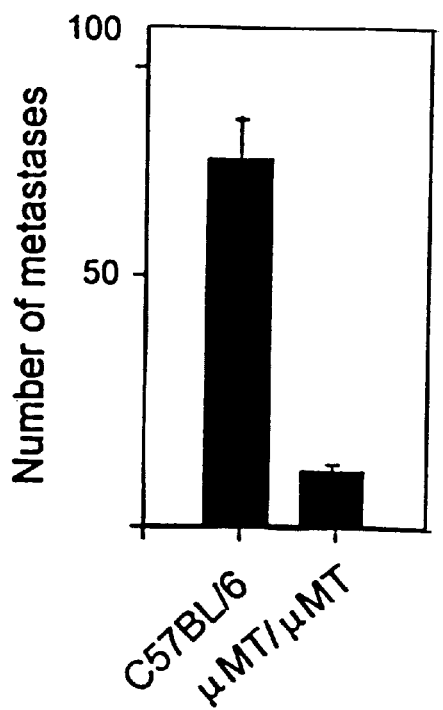
FIG. 2 is a bar graph illustrating the average number of lung metastases in B cell deficient (C57B/μMT/μMT) mice as compared to B cell competent (C57BL/6) mice.

Lung metastases formation involves cell arrest (non-anchorage conditions), extravasation (anchorage condition) and colony formation (anchorage/non-anchorage conditions). To assess whether B cells are effector cells (at least in part) of a metastatic effect, a model for metastatic growth was used. It is known by those skilled in the art that injection of B16F10 cells via the tail vein of mice typically results in the formation of lung metastases. One group of C57BL/6 mice was injected via the tail vein with $10^6$ B16F10 cells. One group of C57 $\mu$MT/$\mu$MT mice was injected via the tail vein with $10^6$ B16F10 cells. Fourteen days postinjection, the lungs from the two groups of mice were evaluated for tumor growth macroscopically, and the number of metastases counted. As shown in FIG. 2, the average number of lung metastases was significantly decreased in B cell deficient (C57 $\mu$MT/$\mu$MT) mice as compared to immunocompetent (C57BL/6) mice. The significant decrease also represents the lack of several of the B cell deficient mice to develop any detectable metastases in the lung. These results confirm the results illustrated in FIG. 1 herein, that there is a decreased ability of B cell deficient mice to mediate tumor progression (including metastasis) as compared to normal mice. In summary, these results are evidence of a subpopulation of B cells are involved in an immune response which can mediate tumor progression.

EXAMPLE 2

Figure 3:
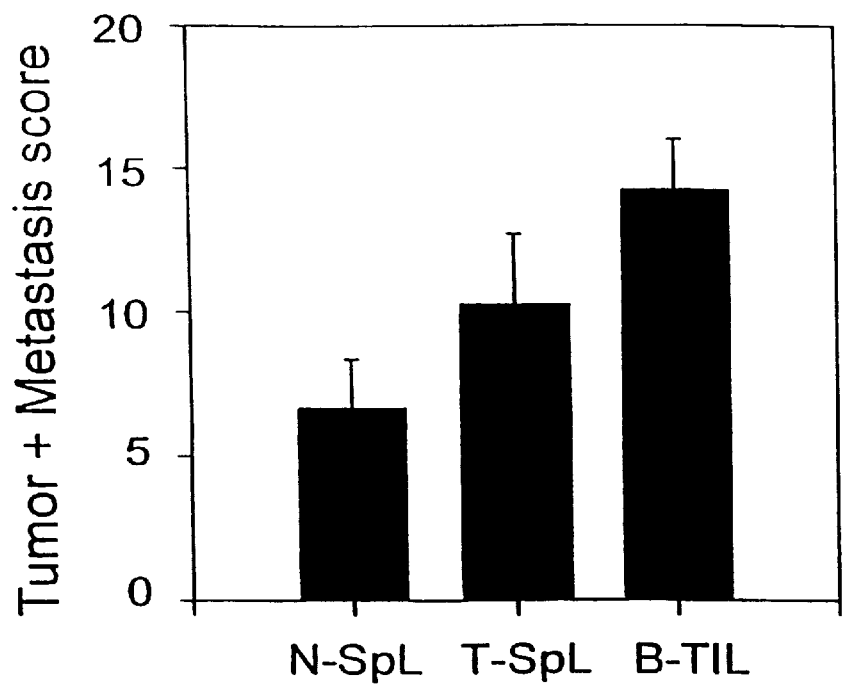
FIG. 3 is a bar graph illustrating in vivo spleen tumor cell growth and liver metastasis (combined score) in the presence of splenic B lymphocytes from tumor bearing mice (T-SpL), B lymphocytes from tumor (B-TIL), and splenic B lymphocytes from normal mice (N-Spl).

To assess whether different populations of B lymphocytes could promote growth of the tumors in vivo, tumor growth in CH3 mammary gland tumor bearing mice was compared when the mice were injected every 2 days for a 14 day period with either B lymphocytes (50,000 cells) isolated from normal mouse spleen; B lymphocytes isolated from lymphoid tissues (e.g., spleens) of tumor bearing mice (50,000 cells), or tumor infiltrating B lymphocytes (B-TIL; 50,000 cells) isolated from tumors of tumor bearing mice. Isolations of B lymphocytes were performed by magnetic separation methods known in the art. After the 14 day period, liver metastasis and spleen tumor growth (tumor+metastasis score) were evaluated and scored. As shown in FIG. 3, B-TIL and B lymphocytes from spleens of tumor bearing mice ("T-Spl") each promoted statistically significant tumor growth and metastasis in vivo, whereas B lymphocytes from normal spleen ("N-Spl") did not enhance either tumor growth or metastasis. An important conclusion that can be drawn from these results is that to gain the ability to promote tumor progression, B lymphocytes must first be exposed to tumor antigens (e.g., prior contact with shed tumor antigen).

EXAMPLE 3

Figure 4:
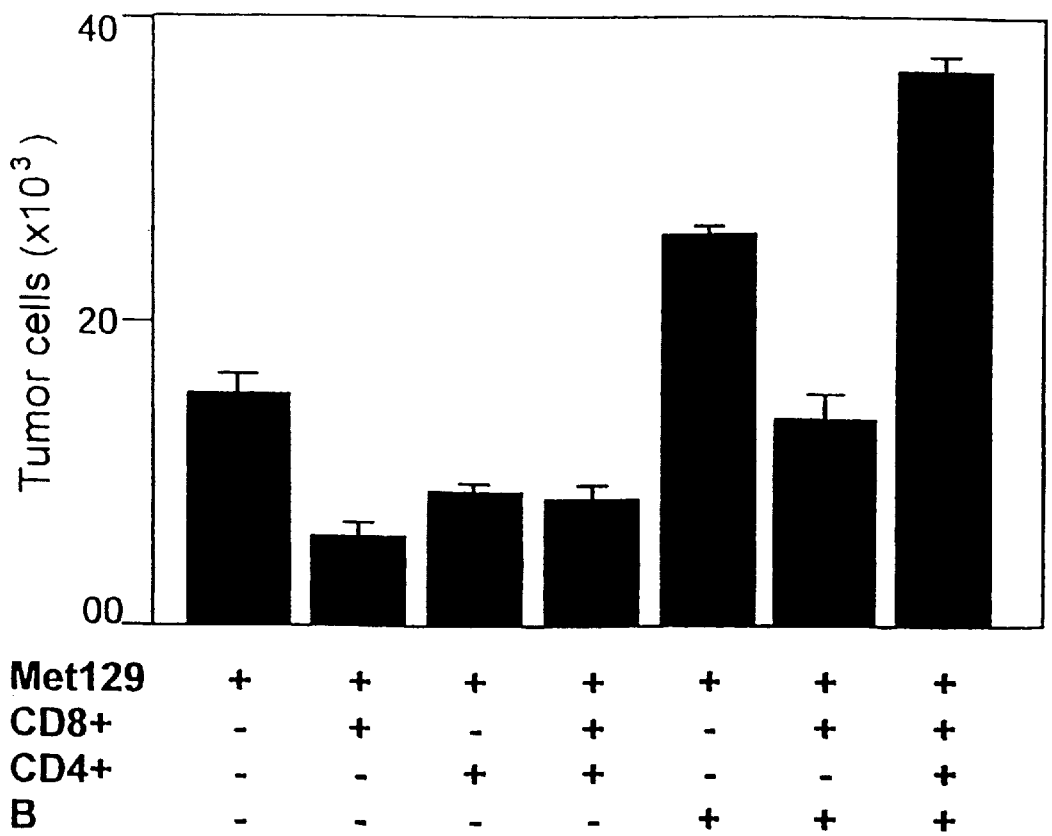
FIG. 4 is a bar graph illustrating in vitro tumor growth of Met 129 tumor cells alone; or co-incubated with either CD8+ cells, CD4+ cells, CD8+ cells and CD4+ cells, B-TIL, CD8+ cells and B-TIL, or B-TIL and CD8+ cells and CD4+ cells.

This Example illustrates that B-TIL promotion of tumor growth in vitro can be mediated via a direct action by B-TIL that does not require a T cell intermediary response; but may also act synergistically with CD4+ T cells, when present. In this illustration, several populations of lymphocytes were isolated using magnetic bead separation techniques from Met 129 tumors removed from C3H mice. Met 129 tumors are high mucin secretors. The lymphocyte populations included tumor infiltrating B lymphocytes (B-TIL), tumor infiltrating CD4+ lymphocytes (CD4+), and tumor infiltrating CD8+ lymphocytes (CD8+). Ten thousand Met 129 cells were cultured in 1.5 ml of tissue culture medium supplemented with 10% fetal bovine serum (FBS) per well in 24 well plates alone, or in the presence of either 10,000 CD8+ cells, in the presence of 10,000 CD4+ cells, in the presence of 10,000 CD8+ cells and 10,000 CD4+ cells, in the presence of 10,000 B-TIL, in the presence of 10,000 B-TIL and 10,000 CD8+ cells, or in the presence of 10,000 CD8+ cells, 10,000 CD4+ cells and 10,000 B-TIL. After 72 hours of co-incubation in monolayer culture, Met 129 tumor cell growth was quantitated using Alcian blue staining; e.g., adherent mucin-producing cells (Met 129 tumor cells) were counted. As shown in FIG. 4, CD8+ cells co-incubated with Met 129 (Met 129+, CD8++, CD4+−, B−) resulted in a statistically significant reduction in tumor cell growth, and thus appeared to effect Met 129 tumor cell death when compared to the control of Met 129 alone (Met 129+, CD8+−, CD4+−, B−). Likewise, a slight reduction in tumor growth or no increase in tumor growth, as compared to the control, was observed when Met 129 tumor cells were co-incubated with either CD4+ cells (Met 129+, CD8+−, CD4++, B−), in the presence of CD8+ cells and CD4+ cells (Met 129+, CD8++, CD4++, B−), or in the presence of B-TIL and CD8+ cells (Met 129+, CD8++, CD4+−, B+). In contrast, statistically significant increased tumor cell growth was observed when B-TIL were co-incubated with Met 129 tumor cells (FIG. 4: Met 129+, CD8+−, CD4+−, B+), and when CD8+ cells, CD4+ cells and B-TIL were co-incubated with Met 129 tumor cells (FIG. 4: Met 129+, CD8++, CD4++, B+), as compared to growth of the control of Met 129 tumor cells alone (Met 129+, CD8+−, CD4+−, B−).

In summary, these results indicate that B-TIL alone can promote tumor growth in vitro via a mechanism involving B-TIL that does not require a T cell intermediary response (FIG. 4: Met 129+, CD8+−, CD4+−, B+). However, it appears that B-TIL may also act synergistically with CD4+ T cells in promoting tumor growth (FIG. 4: Met 129+, CD8++, CD4++, B+). In that regard, it is interesting to note that CD4+ cells alone could not exert a significant tumor promoting effect, but CD4+ cells in combination with B-TIL and CD8+ cells mediated greater tumor progression than did B-TIL alone. Further experiments have identified V$\alpha$3+, CD4+ cells as CD4+ effectors which can promote tumor growth.

EXAMPLE 4

In this illustration, an immunotherapeutic agent was administered to a tumor bearing animal, wherein the immunotherapeutic agent is one which would target B cells to interrupt the host B cell intermediary (pro-tumor) response in a tumor bearing animal, thereby affecting tumor progression. Fifty three C3H mice were injected intrasplenically with $10^6$ Met 129 tumor cells. The injected mice were then divided into two treatment groups. One group of 28 mice was injected with an irrelevant (not directed against any specific mouse antigen) goat IgG antibody (170 $\mu$g per injection) at days 5, 7, and 9 following tumor challenge. A second group consisted of 25 mice injected with goat anti-mouse IgG and goat anti-mouse IgM (170 $\mu$g per injection) at days 5, 7, and 9 following tumor challenge. The goat anti-mouse IgG and IgM antibody used to deplete the C3H mice of their B cells, thereby interrupting the host B cell-mediated pro-tumor immune response. At 22 days following tumor challenge, the two groups of mice were analyzed for primary tumor growth in the spleen, metastasis to the liver, and extra-regional metastasis (abdominal lymph nodes). Table 2 shows one experiment in which compared was primary tumor growth, and the incidence of liver metastasis ("Liver Met.") and extra-regional metastasis ("Extra-R Met.") in the mice treated with irrelevant goat IgG ("Goat-IgG"), and mice treated with goat anti-mouse IgG and goat anti-mouse IgM ("Anti-IgG Anti-IgM"). Table 2 shows that there is a statistically significant reduction in the incidence of metastasis in the immunotherapeutically treated (B cell-depleted) mice ("Anti-IgG Anti-IgM") as compared to the control group receiving irrelevant IgG.

TABLE 2

| Observed | Goat-IgG Control | Anti-IgG Anti-IgM |
| --- | --- | --- |
| Tumor | 8 of 8 | 6 of 6 |
| Liver Met. | 5 of 8 | 0 of 6 |
| Extra-R Met. | 6 of 8 | 0 of 6 |

Figure 5:
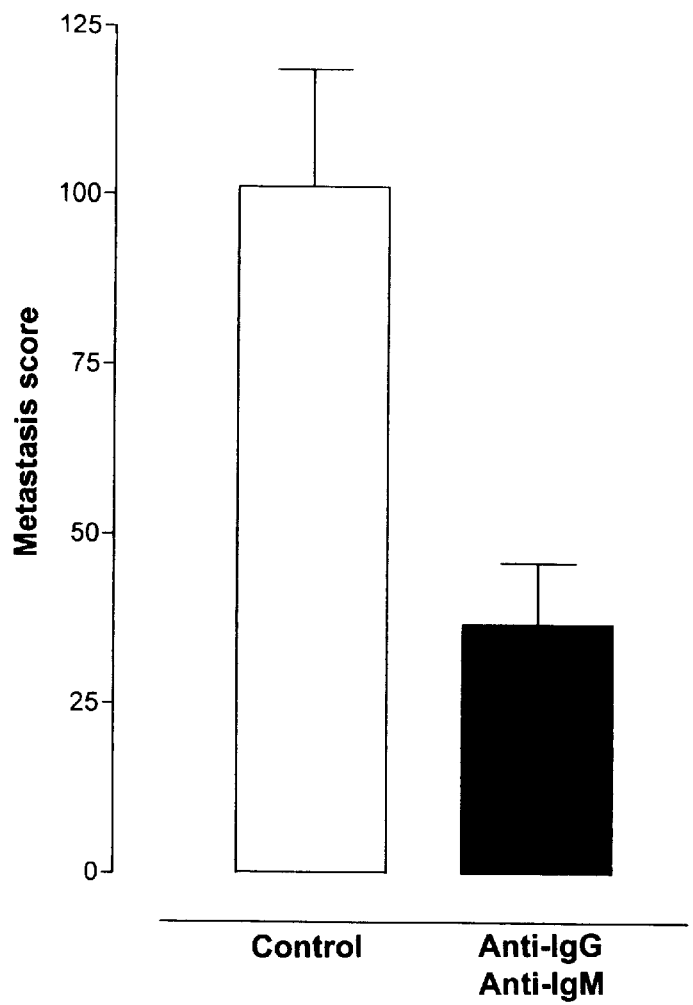
FIG. 5 is a bar graph illustrating the extra-regional (lymph node) and liver metastases scores (combined as "metastasis score") in mice treated with either irrelevant goat IgG, or goat anti-mouse IgG and goat anti-mouse IgM.

Spleen tumor was scored and compared among the two groups of mice. Treatment of the tumor bearing mice with either goat IgG, or goat anti-mouse IgG and goat anti-mouse IgM antibody, had little effect on the growth of the primary tumor in the spleens. In contrast, as shown in FIG. 5, mice receiving immunotherapeutic treatment with goat anti-mouse IgG and goat anti-mouse IgM antibody, thereby having a relative B cell depletion as compared to the control group, showed a statistically significant reduction in the incidence of extra-regional metastasis and liver metastasis as compared to the extra-regional metastasis and liver metastasis exhibited by the control group of mice treated with irrelevant goat IgG. The results in FIG. 5 are normalized values from two experiments. It is important to note that at least 50% of the mice receiving immunotherapeutic treatment with goat anti-mouse IgG and goat anti-mouse IgM, and hence having a relative B cell depletion, did not develop detectable metastases.

In summary, the results illustrated in Table 2, and FIG. 5 further support the finding that a host B cell response (B cell involvement in a pro-tumor immune response) is required for statistically significant promotion of tumor progression. Additionally, the results illustrated in Table 2, and FIG. 5 further support methods and compositions for treating a pro-tumor immune response according to the present invention, wherein the treatment comprises administering an immunotherapeutic composition to effect a B cell depletion in a tumor bearing individual having a pro-tumor immune response, or in an individual having a pro-tumor immune response and from whom the primary tumor has been removed or treated.

EXAMPLE 5

In this Example is illustrated the relative number of memory B cells contained in various locations in humans having a pro-tumor immune response or a pro-tumor immune response and clinically evident solid, non-lymphoid tumor. In this embodiment, memory B cells (CD19+ CD21+) may be expressed in relation to the total number of B cells (e.g., CD19+). Analysis was by flow cytometry, using standard methods, wherein parameters utilized were light scatter used to gate on (select for) lymphocytes based on the size, granularity and cell volume of the lymphocytes; and fluorescent emission from the respective fluorescent labeled antibodies used to detect B lymphocyte subpopulations. Mononuclear cells were isolated from the clinical samples using a density gradient medium and by density gradient centrifugation. Aliquots, each of approximately 1 million cells, were treated in one of several different ways. A first aliquot of cells was left unstained, so as to act as a control for possible auto-fluorescence. A second aliquot of cells was mixed in a staining process with isotype detector molecules. A third aliquot of cells was stained with one or more detector molecules having binding specificity for B cells (single staining with anti-CD19 antibody labeled with Pe-Cy5) or for memory B cells (e.g., double-staining with anti-CD19 antibody labeled with Pe-Cy5, and an anti-CD21 antibody labeled with FITC). When memory B cells were quantitated by double-staining (e.g., for CD19 and CD21), the analysis was gated on those cells positive for CD19 expression as determined by detection of Pe-Cy5 fluorescent emission. CD19 positive lymphocytes were considered to represent the relative total population of B cells in the clinical sample analyzed. CD19 positive lymphocytes were then gated for those cells also positive for CD21 expression as determined by detection of FITC fluorescent emission. Lymphocytes double stained for both CD19 and CD21 were considered to represent memory B cells. Such CD19+, CD21+ memory B cells were then expressed as a percentage of total B cells by using the formula:

(the relative number of CD19+, CD21+ memory B cells/relative number of CD19+ B cells)×100.

Table 3 shows the total number of CD19+ B cells (including memory B cells and other B cell populations expressing CD19, and expressed as a percentage of the total of white blood cells) in the peripheral blood of individuals having solid, non-lymphoid tumor and a pro-tumor immune response ("Tumor/PTIR") as compared to a percentage of CD19+ B cells from the peripheral blood of apparently healthy individuals ("Baseline control"). As shown in Table 3, the mean percentage±standard error of the mean (Mean %±SEM) for peripheral blood CD19+ B cells from individuals having solid, non-lymphoid tumor and a pro-tumor immune response is 2.7±0.5; whereas the Mean %±SEM for peripheral blood CD19+ B cells from apparently healthy individuals is 12.7±3.6. Thus, there is a statistically significant (P value=0.0001) decrease in the relative percentage of total (CD19+) B cells in individuals having a pro-tumor immune response as compared to the values in individuals who lack a pro-tumor immune response. Table 3 also shows the percentage of CD19+, CD21+ B cells from the peripheral blood of individuals having solid, non-lymphoid tumor and a pro-tumor immune response ("Tumor/PTIR") as compared to a percentage of CD19+, CD21+ B cells from the peripheral blood of apparently healthy individuals ("Baseline control"). As shown in Table 3, the mean percentage±standard error of the Mean %±SEM for peripheral blood memory B cells from individuals having solid, non-lymphoid tumor and a pro-tumor immune response is 58.2±5.2; whereas the Mean %±SEM for peripheral blood memory B cells from apparently healthy individuals is 22.0±3.6. Thus, there is a statistically significant (P value<0.0001) increase in the relative percentage of memory B cells in individuals having a pro-tumor immune response as compared to the values in individuals who lack a pro-tumor immune response. Using similar methods as described herein, other altered B cell phenotypes were determined from peripheral blood of individuals having tumor and a pro-tumor immune response ("Tumor/PTIR") as compared to peripheral blood control values ("Baseline control"). Note that B cells hyper-expressing CD21 (CD21++ cells) were distinguished from CD21+ B cells by setting as a lower limit of the range of CD21++ a value which is higher than 95% of the CD21+ values as expressed by B cells of apparently healthy controls. Table 3 shows that altered B cell phenotype comprising peripheral blood CD19+ CD21+ B cells, CD19+ CD21++ B cells, CD19+ sTn+ B cells, and CD19+ CD5+ sTn+ B cells, and a combination thereof, is increased in amount compared to the respective relative baseline control. Further, CD19+ B cells are decreased in amount as compared to the baseline control. Hence, such altered B cell phenotype comprise indicators or parameters for the presence of a pro-tumor immune response (alone or with solid nonlymphoid tumor).

TABLE 3

| B cell subpopulation | Baseline control | Tumor/PTIR |
| --- | --- | --- |
| CD19+ | 12.7 ± 3.6 | 2.7 ± 0.5 |
| CD19+ sTn+ | 1.3 ± 0.4 | 5.9 ± 1.5 |
| CD19+ CD21+ | 22.0 ± 3.6 | 58.2 ± 5.2 |
| CD19+ CD21++ | 3.8 ± 1.8 | 48.8 ± 5.3 |
| CD19+CD21+sTn+ | 29.7 ± 5.0 | 16.1 ± 3.7 |
| CD19+ CD5+ | 1.8 ± 0.9 | 2.4 ± 1.1 |
| CD19+CD5+sTn+ | 0.3 ± 0.1 | 29.0 ± 6.3 |

EXAMPLE 6

In the previous Examples, it was illustrated that a host B cell response is involved in a pro-tumor immune response which mediates tumor progression and metastasis. These findings in an individual are indicative of one or more subpopulations of B cells as being beneficial for progression; and therefore, detrimental to the individual's prognosis. In such an individual, the B cells may be found in various body tissues. In one embodiment of a method of treating a pro-tumor immune response according to the present invention, administered to an individual is a therapeutically effective amount of an immunotherapeutic composition for depleting B cells that may be present in one or more tissues or fluids of the individual, such as lymphoid tissues (e.g., either regional and/or distal relative to the site(s) of solid nonlymphoid tumor), or solid, nonlymphoid tumor, or body fluids such as peripheral blood, or a combination thereof. The administered immunotherapeutic composition subsequently comes in contact with such B cells, and, may result in one or more therapeutic functions. The one or more therapeutic functions may include, but is not limited to: B cell depletion; inhibition of proliferation of B cells involved in a pro-tumor immune response; inhibition of the differentiation of B cells into plasma cells which secrete anti-shed tumor antigen antibody; reducing the number of naïve B cells that could be activated by shed tumor antigen; and causing or inducing depletion of one or more B cell subpopulations that may be involved in a pro-tumor immune response. Thus, a therapeutically effective amount of the immunotherapeutic composition contacts and binds to one or more determinants on B cells to cause or enable B cell depletion, thereby immunomodulating the immune system to inhibit the tumor-promoting function of B cells involved in a pro-tumor immune response. Inhibiting the tumor-promoting function of B cells involved in a pro-tumor immune response may also inhibit tumor progression.

Lymphoid tissues and solid, nonlymphoid tumors often are proximal to one or more vessels (blood or lymphatic) that access (feed or extend through) the tissue, or organ in which is situated the tumor. Thus, to deplete B cells in such lymphoid tissues and/or solid, nonlymphoid tumor, administered is a therapeutically effective amount of the immunotherapeutic composition into a blood vessel or lymphatic vessel in a site-directed method of delivery to treat a pro-tumor immune response. In one example, a catheter may be inserted into one or more of the major vessels (blood or lymphatic) that access the lymphoid tissue and/or the organ containing the solid, nonlymphoid tumor to be targeted, using standard methods for inserting the catheter into such vessels, as known to those skilled in the art. Vessels that access the lymphoid tissues and/or solid, nonlymphoid tumor may include vessels accessing organs that are foci of solid, non-lymphoid tumor and/or a pro-tumor immune response. In another example, controlled and site-directed delivery of the immunotherapeutic composition may be achieved by infusing, such as by a catheter or functionally similar means, a therapeutically effective amount of the composition into one or more vascular accesses that directly supplies the targeted lymphoid tissues and/or the solid, nonlymphoid tumor. The delivered immunotherapeutic composition may then concentrate primarily in the lymphoid tissue and/or the solid, nonlymphoid tumor; and more specifically to the B cells present, by the binding between the affinity ligand of the immunotherapeutic composition and its target determinant on the B cells. Site-directed delivery of the immunotherapeutic composition does not rule out that a portion of the immunotherapeutic composition may gain access to peripheral blood, and any benefit associated therewith.

The basic principle underlying this site-directed treatment of a pro-tumor immune response, comprising B cell involvement in progression of solid nonlymphoid tumors, according to the present invention involves introducing a therapeutically effective amount of the immunotherapeutic composition into a vascular or lymphatic access of a tissue that is a foci of tumor and/or a pro-tumor immune response. As previously described herein, the tissue may comprise lymphoid tissue, solid nonlymphoid tumor, an organ containing the solid, non-lymphoid tumor, and a combination thereof. The immunotherapeutic composition may be administered by itself, or in conjunction with other anti-cancer treatments (e.g., chemotherapy, treatment with anti-inflammatory agents, radiation therapy, immunotherapy, surgery, and the like). As known to those skilled in the art, methods of site-directed delivery have been used in anticancer therapy. Infusion of chemotherapeutic agents comprising cytotoxic drugs into arteries supplying a targeted tissue in a cancer patient has resulted in significant clinical benefit. For example, hepatic arterial infusion of fluoropyrimidines resulted in superior tumor response in patients as compared to the classical strategy of intravenous chemotherapy (*J. Natl. Cancer Inst.*, 1996, 88:252–8). The site-directed immunotherapy of the present invention has the added advantage in that, via the binding specificity of the affinity ligand, a therapeutically effective amount of the immunotherapeutic composition may be substantially arrested in the targeted tissue by binding to a B cell determinant. The immunotherapeutic composition may further comprise a pharmaceutically acceptable carrier for facilitating infusion into the vascular or lymphatic access of the individual's tissue(s) to be targeted.

For example, in treating a pro-tumor immune response that is directed to B cells that may be involved in a pro-tumor immune response and that may be found in lymphoid tissues regional to the liver and/or solid, nonlymphoid tumor in the liver with the immunotherapy according to the present invention, a catheter may be inserted percutaneously into the main hepatic artery, or an accessory hepatic artery, branches thereof, or a vein supplying the liver (portal vein), wherein the catheter is inserted via the femoral artery such as under image intensification (see, e.g., Shepherd et al., 1987, *J. Clin. Oncol.* 5:635–40; Takagi et al., 1983, *J. Surg. Oncol.* 23:219–22). Where the B cells may be present in lymphoid tissues regional to the lung, and/or solid, nonlymphoid tumor in the lung with the immunotherapeutic composition according to the present invention, a catheter may be inserted into the pulmonary artery, or an accessory artery or branches thereof, wherein the catheter is inserted using standard methods for inserting the catheter into such vasculature, as known to those skilled in the art. In targeting lymphoid tissues directly with the immunotherapeutic composition for treating a pro-tumor immune response according to the present invention, a catheter may be inserted into one or more of the major nodal arteries or lymphatic vessels that supply the lymphoid tissue, or an accessory or branches thereof, wherein the catheter is inserted using standard methods for inserting the catheter into such vessels, as known to those skilled in the art. In any of the above examples, the treatment may further comprise multiple infusions of a therapeutically effective amount of the immunotherapeutic composition over time, as monitored by treatment response and by indicia of local toxicity, or atrophy, or of a therapeutic effect. Further, the catheter may be operatively connected to a portable pump such that the immunotherapeutic composition may be administered intermittently or continuously. As apparent to those skilled in the art, what constitutes a "therapeutically effective amount" of the immunotherapeutic composition will depend upon such factors which include, but are not limited to, size and weight of the individual to be treated, stage of disease progression in the individual to be treated, affinity and avidity of the affinity ligand for the B cell determinant, amount or degree of B cell involvement in a pro-tumor immune response at the time of treatment, the size and location of the vascular access for delivering the immunotherapeutic composition to the targeted tissue of the individual, and the mode of administration for the site-directed delivery.

EXAMPLE 7

In this example, illustrated is an embodiment of treating B cell involvement in a pro-tumor immune response according to the present invention, wherein a therapeutically effective amount of the immunotherapeutic composition is administered in conjunction with chemotherapy in a site-directed delivery. The general objectives of this combined therapy are to reduce or arrest the growth of the residual mass of the solid, nonlymphoid tumor, and to cause B cell depletion. For example, site-directed treatment of recurrent colorectal cancer may comprise combined therapy comprising regional chemotherapy, and treatment of a pro-tumor immune response with the immunotherapeutic composition according to the present invention. In another example, site-directed treatment of recurrent colorectal cancer may comprise combined therapy comprising treatment with a pharmaceutically effective amount of an anti-inflammatory agent, and treatment of a pro-tumor immune response with a therapeutically effective amount of an immunotherapeutic composition according to the present invention. In one embodiment, the combined therapy is administered to an individual after surgery, wherein surgery comprised an incomplete tumorectomy, and wherein liver metastases still remain.

To illustrate such combined therapy, and using methods known to those skilled in the art, administered through a catheter is (a) a pharmaceutically effective amount of a chemo-therapeutic drug combination, and (b) a therapeutically effective amount of the immunotherapeutic composition, in a process known as hepatic arterial infusion. Alternatively, the hepatic artery may be chemo-embolized (thereby temporarily blocking off the blood flow to the liver), so that the combined therapy is substantially localized to the liver and lymphoid tissues regional to the liver. Hepatic arterial infusion and hepatic arterial chemo-embolization are standard methods used in the treatment of liver metastases from colorectal cancer and from breast cancer. In an embodiment of the combined therapy wherein hepatic chemo-embolization is performed, the one or more chemo-therapeutic agents is administered in conjunction with a embolic agent as known to those skilled in the art.

Figure 7:
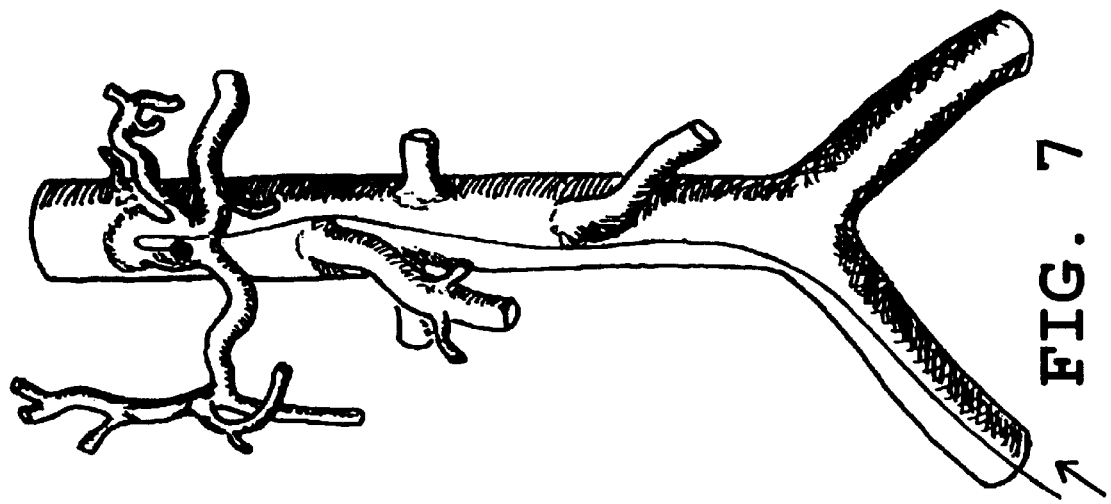
FIG. 7 is a graphic illustration of site-directed delivery of the immunotherapeutic composition using catheterization via the celiac trunk to the common hepatic artery.
Figure 6:
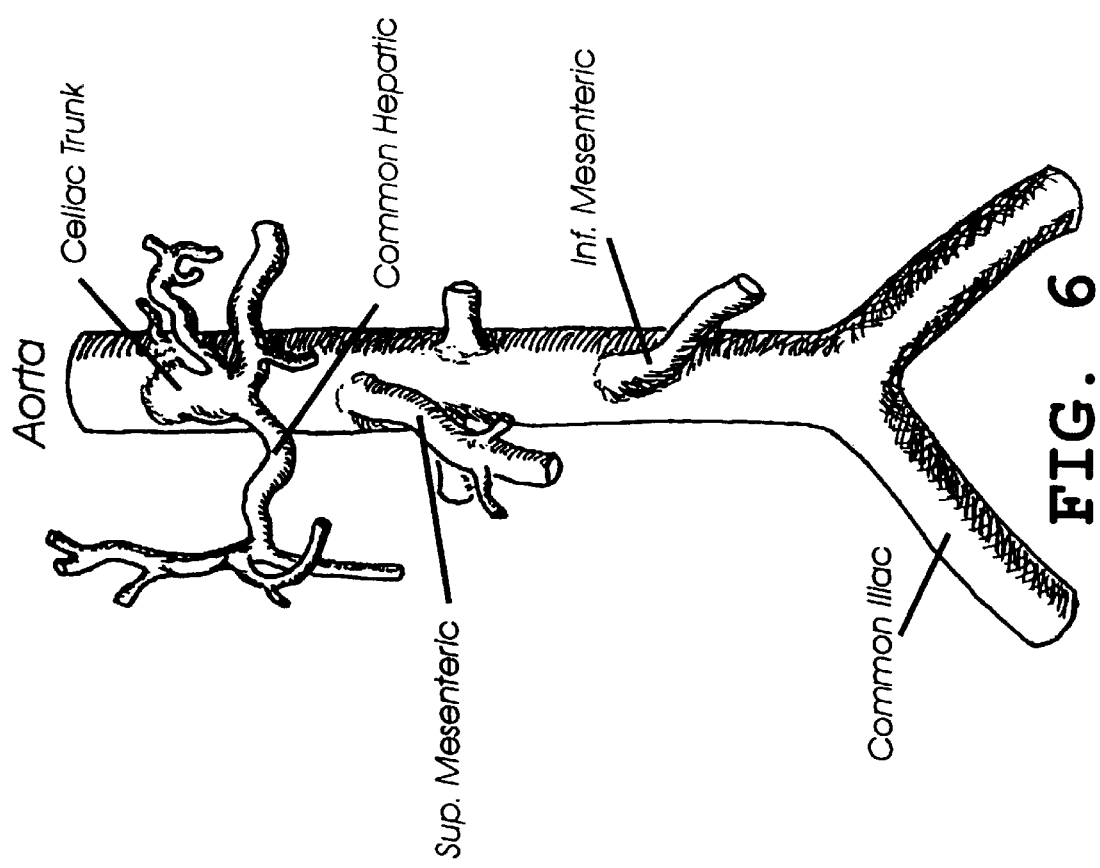
FIG. 6 is a graphic illustration of exemplary arteries and arterial branches useful for site-directed delivery of the immunotherapy.
Figure 8A:
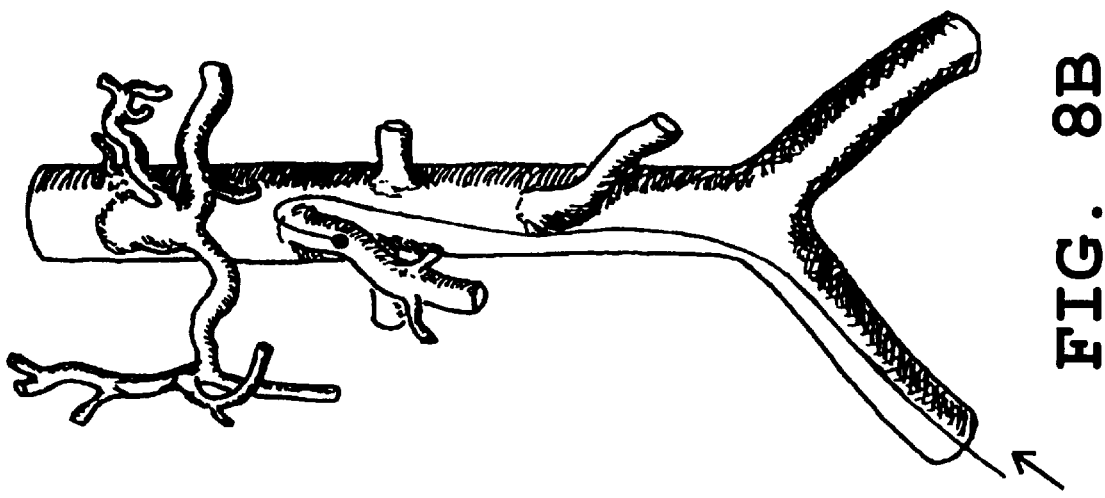
FIG. 8A is a graphic illustration of site-directed delivery of the immunotherapeutic composition using catheterization via the celiac trunk to the common hepatic artery, which may be used in conjunction with the delivery in FIG. 8B.
Figure 8B:
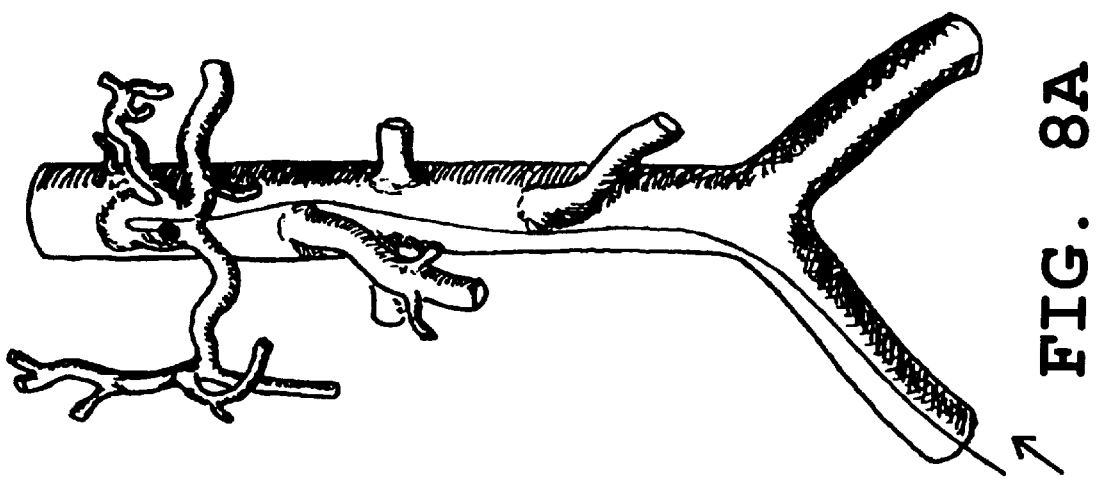
FIG. 8B is a graphic illustration of a further embodiment of site-directed delivery of the immunotherapeutic composition using catheterization via the superior mesenteric artery.
Figure 10:
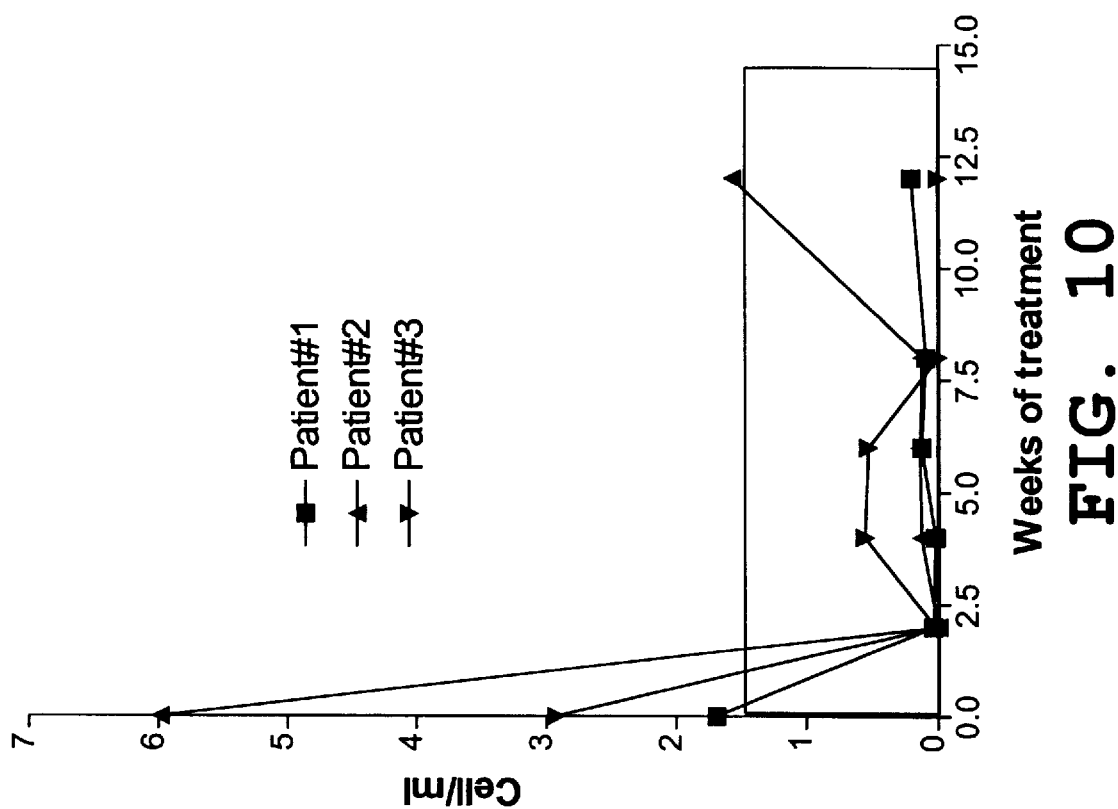
FIG. 10 is a graph showing the depletion of CD19+ sTn+ B cells effected by treatment of individuals with an immunotherapeutic composition.

As to the combined therapy, there are various chemo-therapeutic agents and anti-inflammatory agents known in the art which may be used. The pharmaceutically effective dosage of these agents depend on factors that may include the properties of the specific agent(s) used (chemical nature, rate of metabolism, rate of clearance, and the like), the tumor type targeted, and physical and metabolic variables associated with the individual receiving treatment. Exemplary combinations and pharmaceutically effective dosages of chemotherapeutic agents known in the art include, but are not limited to, a combination of cisplatin (e.g., 122 mg), mitomycin C (e.g., 15 mg), doxorubicin (e.g., 55 mg), and 5-fluorouracil (5FU; e.g., 900 mg); doxorubicin (e.g., 30 mg), cisplatin (e.g., 100 mg) and mitomycin C (e.g., 30 mg); pirarubicin (THP) and lipiodol emulsion; 5FU-lipiodol emulsion; epirubicin, cisplatin, and lipiodol emulsion; adriamycin (e.g., 40–50 mg) and lipiodol; and irinotecan hydrochloride (CPT11, e.g., 50–60 mg) in combination with either 5-FU or cisplatin or carboplatin or etoposide. FIG. 6 illustrates arteries which may be accessed by catheter for site-directed delivery of a therapeutically effective amount of the immunotherapeutic composition (by itself or as part of combined therapy) to tissues (e.g., solid, nonlymphoid tumors and/or lymphoid tissues) in the regions of the abdomen and colon. FIG. 7 illustrates site-directed delivery of a therapeutically effective amount of an immunotherapeutic composition (by itself or as part of combined therapy) to tissues (e.g., solid, nonlymphoid tumors and/or lymphoid tissues) in the region of the abdomen only, using catheterization into the common hepatic artery via the celiac trunk. FIGS. 8A and 8B illustrate site-directed delivery of a therapeutically effective amount of an immunotherapeutic composition (by itself or as part of combined therapy) to tissues (e.g., solid, nonlymphoid tumors and/or lymphoid tissues) in the regions of the abdomen and colon, using catheterization into the common hepatic artery via the celiac trunk (FIG. 8A), and via the same catheter, administered through the superior mesenteric arteria (FIG. 8B).

In continuing with this example, administered to an individual having residual colorectal cancer with liver metastases is a pharmaceutically effective amount of a chemotherapeutic agent combination comprising adriamycin (100 mg), cisplatin (50 mg), and mitomycin C (10 mg), via intra-arterial chemo-embolization, and a therapeutically effective amount of the immunotherapeutic composition comprising a chimeric anti-CD20 mAb (RITUXAN™; see, e.g., U.S. Pat. No. 5,736,137; e.g., 40 mg), into the common hepatic artery via the celiac trunk; and via the same catheter, administered through the superior mesenteric arteria, is the chimeric anti-CD20 mAb (60 mg). The same or similar procedure may be repeated (e.g., twice at approximately 5 weeks apart). Various parameters may be used to monitor the effect of such combined therapy. For example, the relative number of one or more peripheral blood B lymphocyte subpopulations (e.g., see Table 3) of the treated individual may be assessed (e.g., weekly, bi-weekly, or monthly). Additionally, the serum concentration of shed tumor antigen, and/or of IgG and IgM anti-shed tumor antigen antibody, and or immune complexes comprising shed tumor antigen complexed to anti-shed tumor antigen antibody, may be assessed (e.g., by an immunoassay), wherein a reduction of one or more of these serological parameters is an indicator of possible therapeutic benefit resulting from the treatment. Also, the CD4/CD8 ratio of peripheral blood lymphocytes may be assessed (e.g., by flow cytometry). Imaging of the tumor (e.g., bimonthly by CT-scan or MRI or PET-Scan) may also be used to assess status of the tumor during and after treatment. Tumor markers (e.g., CEA and CA19.9) found in the peripheral blood may also be used to assess status of the tumor during and after treatment. As will be apparent to one skilled in the art, essentially the same procedures outlined above (for treatment of an individual having residual colorectal cancer with liver metastases) may be used to treat an individual for treatment of recurrence of colorectal tumor with liver metastases.

EXAMPLE 8

In this example, illustrated is an embodiment of treating B cell involvement in a pro-tumor immune response according to the present invention, wherein a therapeutically effective amount of the immunotherapeutic composition is administered to an individual having, or are suspected of having, a pro-tumor immune response. Individuals who may be included in this type of protocol may be individuals having a pathology selected from the group consisting of pre-cancerous lesions, early stage cancer (Stage I or Stage II solid, nonlymphoid tumors); advanced cancer (solid, nonlymphoid tumors and their metastases—Stage III or Stage IV); parameters which are indicators of a pro-tumor immune response (see, e.g., Table 3 herein); or those who are in apparent remission of a solid, nonlymphoid tumor. The objective of this B cell treatment is to cause B cell depletion. For the individual having either early stage cancer or advanced cancer, B cell depletion comprises reducing the number of B cells present in a tissue or fluid selected from the group consisting of lymphoid tissues (e.g., either regional and/or distal relative to the site(s) of solid, nonlymphoid tumor), solid, nonlymphoid tumor, a body fluid such as peripheral blood, or a combination thereof. For individuals who are in apparent remission of a solid, nonlymphoid tumor, B cell depletion comprises reducing the number of B cells present in a fluid or tissue selected from the group consisting of peripheral blood, lymphoid tissues which are regional to the sites where the solid, nonlymphoid tumor existed at one time, but at which there is no apparent tumor at the time of treatment, and a combination thereof. For the individual having parameters of a pro-tumor immune response, and no clinical evidence of solid, nonlymphoid tumor, B cell depletion comprises reducing the number of B cells present in a fluid or tissue selected from the group consisting of peripheral blood, lymphoid tissues which contain shed tumor antigen, and a combination thereof. The immunotherapeutic composition may be administered to the individual in any one or more modes which may be used to achieve the objective of this B cell treatment. In a preferred embodiment, the administration of a therapeutically effective amount of the immunotherapeutic composition to an individual, in performing the method according to the present invention, is parenteral. The term "parenteral" includes administration intravenously, intramuscularly, subcutaneously, rectally, vaginally, or intraperitoneally. The most preferred parenteral administration is intravenous administration. Alternatively, and as previously described in more detail herein, administration of a therapeutically effective amount of the immunotherapeutic composition to an individual, in performing the method according to the present invention, may be site-directed by use of catheterization or functionally similar means.

For example, for an individual who has advanced colorectal cancer, or for an individual who is in apparent remission of colorectal cancer, or in an individual having parameters indicative of the presence of a pro-tumor immune response, administered to the individual is a therapeutically effective amount of the immunotherapeutic composition. As will be apparent to one skilled in the art, a therapeutically effective amount (effective dosage), and whether repeated dosages may be warranted, will depend on such factors as the stage of development of the pro-tumor immune response, overall health of the individual to be treated, other treatments which the individual may be undergoing, and pharmacokinetic properties of the type of the immunotherapeutic composition being used. For example, for an immunotherapeutic composition comprising a chimeric anti-CD20 mAb, a therapeutically effective dose may range from about 0.01 mg/kg of body weight to about 40 mg/kg of body weight. However, as apparent to one skilled in the art, and in the discretion of a medical practitioner, a treatment may be warranted with a dosage falling inside or outside of this illustrative range.

In an illustration of parenteral administration, a therapeutically effective amount of the immunotherapeutic composition comprising a chimeric anti-CD20 mAb may be administered by intravenous injection. In an illustrative alternative embodiment comprising a site-directed administration, a therapeutically effective amount of the immunotherapeutic composition comprising a chimeric anti-CD20 mAb (e.g., 40 mg) is administered through a catheter via the celiac trunk; and via the same catheter, administered through the superior mesenteric arteria, is a therapeutically effective amount of the immunotherapeutic composition comprising chimeric anti-CD20 mAb (e.g., 60 mg). In either illustrative embodiment, the dosage may be repeated, depending upon changes in the tumor status, and measurable parameters of efficacy of the treatment. Various parameters may be used to monitor the effect of treating B cells in the treated individual; wherein the parameters may include, but are not limited to, relative counts of peripheral blood B lymphocyte subpopulations (e.g., see Table 3), serum concentration of shed tumor antigen and/or of IgG and IgM anti-shed tumor antigen antibody and/or immune complexes comprised thereof, blood tumor markers, and imaging of the nonlymphoid tumor (e.g., to assess tumor status in the individuals with such advanced cancer) after each dosage or series of dosages comprising the treatment.

Figure 9:
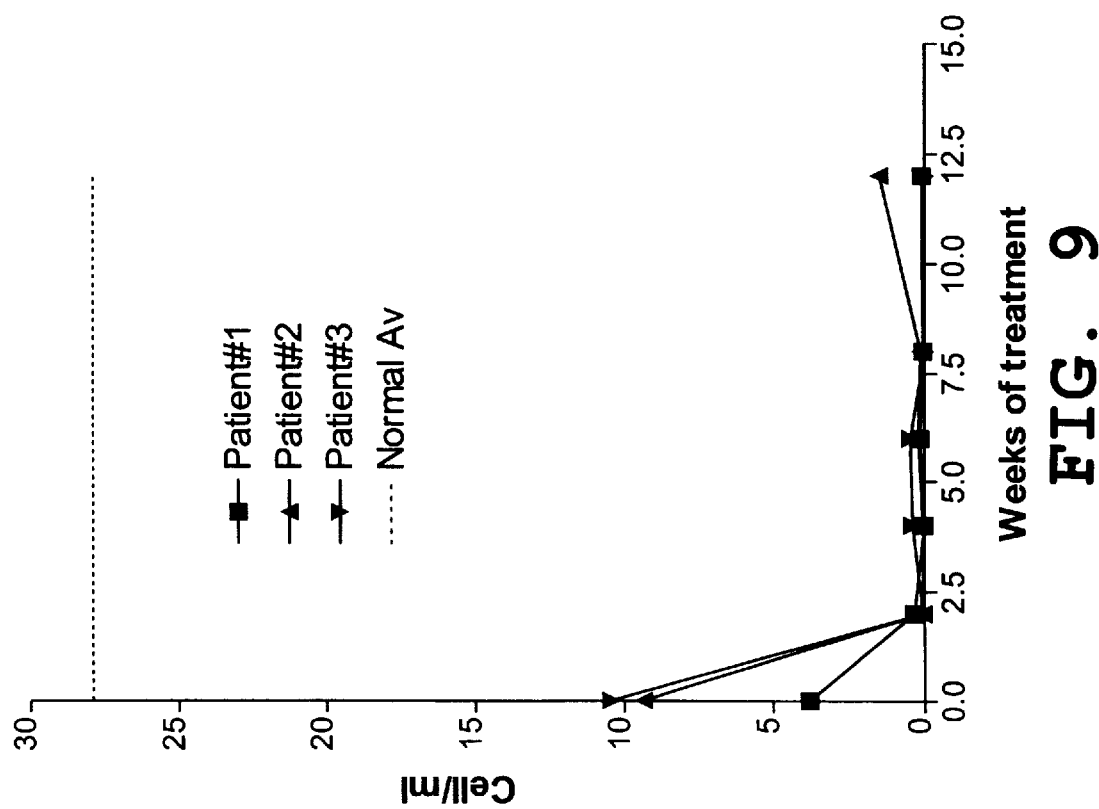
FIG. 9 is a graph showing the depletion of CD19+ B cells effected by treatment of individuals with an immunotherapeutic composition.
Figure 13:
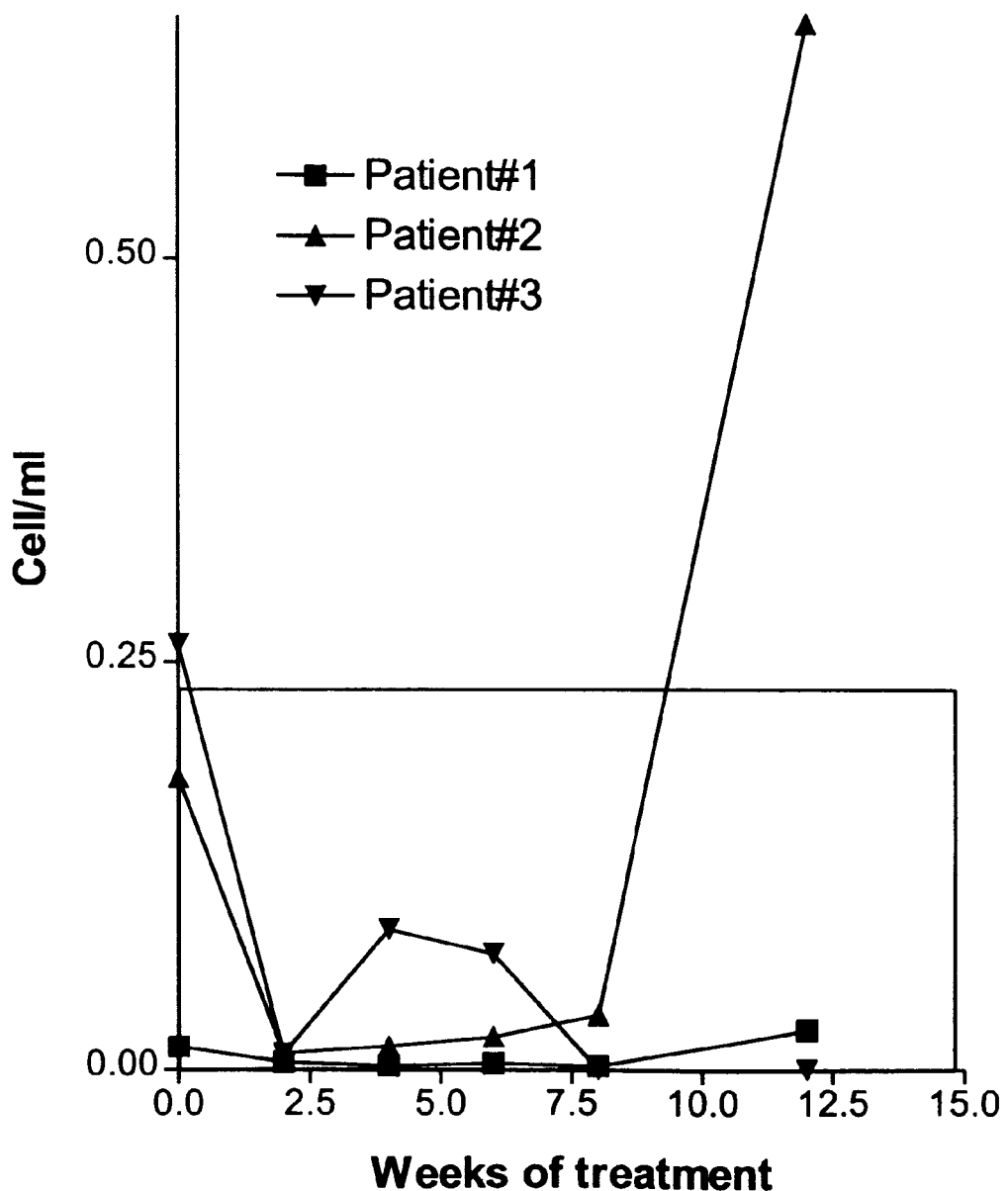
FIG. 13 is a graph showing the depletion of CD19+ CD5+ B cells effected by treatment of individuals with an immunotherapeutic composition.

To illustrate an embodiment of the method of treating B cells according to the present invention, administered to individuals having advanced cancer (Stage IV, solid, nonlymphoid tumor) and a pro-tumor immune response was a therapeutically effective amount of an immunotherapeutic composition comprising a chimeric anti-CD20 mAb. To each individual was administered, by intravenous infusion, an initial dosage of 200 mg of the immunotherapeutic composition; and then administered were two additional infusions spaced apart by four weeks. Thus, three complete infusions were administered: the initial treatment (week 0), one at week 4, and one at week 8. Generally, the first infusion was at an initial rate of about 50 mg/hour; however, additional infusions were administered at a faster rate which was dependent on how the individual tolerated infusion, the treating physician's judgment, drug manufacturer's instructions, and lack of side effects. As shown in FIGS. 9–13, treatment according to the present invention of 3 individuals (■, ▲, ▼) with a therapeutically effective amount of the immunotherapeutic composition resulted in a depletion in overall B cells (CD19+ cells; FIG. 9) and B1 cells (CD19+ CD5+ cells; FIG. 13), and normalization of the amounts of B cell subpopulations comprising altered B cell phenotype (FIG. 10, CD19+ sTn+ cells; FIG. 11, CD19+ CD21+ sTn+ cells; and FIG. 12, CD19+ CD21+ cells) to within a range observed in apparently healthy individuals. Such an observed effect of the immunotherapeutic composition on altered B cell phenotypes in a treated individual may be an indicator that depletion of B cells may result in a therapeutic benefit to the treated individual.

Figure 14:
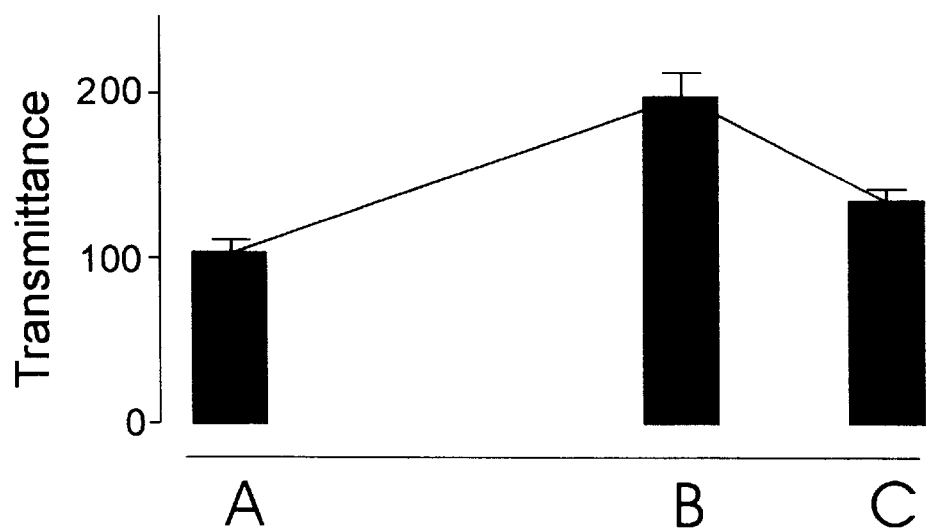
FIG. 14 is a bar graph showing the change in density of metastases as effected by treatment of an individual with an immunotherapeutic composition.

Clinical evaluation of individuals treated with the method according to the invention, such as by an embodiment illustrated above, has indicated that depletion of B cells can result in a therapeutic benefit to the treated individual. For example, one of the treated individuals whose B cell depletion is noted in FIGS. 9–13, underwent imaging of the individual's liver metastases before, and after, treatment according to a method of the present invention. The imaging results of the metastases before treatment, as compared to those after treatment, revealed that the liver metastases did not significantly change in diameter or mass. However, as shown in FIG. 14, a significant change in density was effected as a result of treatment. In FIG. 14, time points A (approximately 8 months before treatment was initiated) & B (just prior to initiation of treatment), and time point C (after a treatment regimen was completed) are plotted versus transmittance of the respective image of the metastases. Treatment reduces the transmittance, and hence indicates an increase in density, as shown by comparing time point C to time point B. Taken together, the increase in density along with the observed dispersal of the metastases and the infiltration of normal tissue into the metastases as evident from imaging at time point C, is an indication that the metastases are undergoing fibrosis as a result of the treatment.

The foregoing description of the specific embodiments of the present invention have been described in detail for purposes of illustration. In view of the descriptions and illustrations, others skilled in the art can, by applying, current knowledge, readily modify and/or adapt the present invention for various applications without departing from the basic concept, and therefore such modifications and/or adaptations are intended to be within the meaning and scope of the appended claims.

What is claimed is:

1. A method for reducing a pro-tumor immune response in an individual, the method comprising administering to the individual a composition, wherein the composition comprises an affinity ligand which selectively binds to a B cell determinant, and wherein the B cells targeted in the method and by the composition are nonmalignant B cells, wherein the composition is administered in an amount effective to deplete said B-cells.

2. The method according to claim 1, wherein the nonmalignant B cells are B cells selected from the group consisting of mature B cells, memory B cells, CD19+ sTn+ B cells, CD19+ CD21+ B cells, CD19+CD21+sTn+ B cells, CD19+ CD5+ B cells, CD19+ CD5+ sTn+ B cells, and a combination thereof.

3. The method according to claim 1, wherein the composition is a chimeric anti-CD20 monoclonal antibody.

4. The method according to claim 1, wherein the composition is administered by a mode selected from the group consisting of parenterally, and in a site directed method in which the composition is delivered to a localized region or a tissue selected from the group consisting of lymphoid tissue, solid nonlymphoid tumor, an organ containing the solid, non-lymphoid tumor, and a combination thereof.

5. The method according to claim 1, wherein the composition further comprises an additional component selected from the group consisting of one or more chemotherapeutic agents, an anti-inflammatory agent, cytolytic agent, a pharmaceutically acceptable carrier, and a combination thereof.

6. The method according to claim 1, further comprising administering to the individual a pharmaceutically effective amount of one or more chemotherapeutic agents.

7. The method according to claim 1, further comprising administering to the individual a pharmaceutically effective amount of an anti-inflammatory agent.

8. A site-directed method for reducing a pro-tumor immune response in an individual, the method comprising: administering to the individual a composition, wherein the composition comprises an affinity ligand which selectively binds to a B cell determinant, wherein the B cells targeted in the method and by the composition are nonmalignant B cells, wherein the composition is administered into a vessel that accesses a tissue, wherein the tissue comprises a tissue selected from the group consisting of lymphoid tissue, solid, nonlymphoid tumor, and a combination thereof, and wherein the composition is administered in an amount effective to deplete said B-cells.

9. The method according to claim 8, wherein the tissue is selected from the group consisting of lymphoid tissue, and a combination of lymphoid tissue and solid, nonlymphoid tumor; and wherein the lymphoid tissue is selected from the group consisting of lymphoid tissue regional to solid, nonlymphoid tumor, lymphoid tissue distal to solid, nonlymphoid tumor, and a combination thereof.

10. The method according to claim 8, wherein the nonmalignant B cells are B cells selected from the group consisting of mature B cells, memory B cells, CD19+ sTn+ B cells, CD19+ CD21+ B cells, CD19+CD21+ sTn+ B cells, CD19+ CD5+ B cells, CD19+ CD5+ sTn+ B cells, and a combination thereof.

11. The method according to claim 8, wherein the composition is a chimeric anti-CD20 monoclonal antibody.

12. The method according to claim 8, wherein the composition further comprises an additional component selected from the group consisting of one or more chemotherapeutic agents, and anti-inflammatory agent, cytolytic agent, a pharmaceutically acceptable carrier, and a combination thereof.

13. The method according to claim 8, further comprising administering to the individual a pharmaceutically effective amount of one or more chemotherapeutic agents.

14. The method according to claim 8, further comprising administering to the individual a pharmaceutically effective amount of an anti-inflammatory agent.

15. The method according to claim 8, wherein a catheter is used for site-directed delivery of the composition to tissues in a region selected from the group consisting of the abdomen, colon, and a combination thereof.

16. The method according to claim 15, further comprising using a catheter to administer a pharmaceutically effective amount of one or more chemotherapeutic agents.

17. The method according to claim 15, further comprising using a catheter to administer a pharmaceutically effective amount of an anti-inflammatory agent.

18. A method for reducing a pro-tumor immune response in an individual, the method comprising administering to the individual a composition, wherein the composition comprises an affinity ligand which selectively binds to a B cell determinant, wherein the B cells targeted in the method and by the composition are nonmalignant B cells, wherein the composition is administered intravenously and wherein the composition is administered in an amount effective to deplete said B-cells.

19. The method according to claim 18, wherein the nonmalignant B cells are B cells selected from the group consisting of mature B cells, memory B cells, CD19+ sTn+ B cells, CD19+ CD21+ B cells, CD19+CD21+ sTn+ B cells, CD19+CD5+ B cells, CD19+ CD5+ sTn+ B cells, and a combination thereof.

20. The method according to claim 18, wherein the composition is a chimeric anti-CD20 monoclonal antibody.

21. The method according to claim 18, wherein the composition further comprises an additional component selected from the group consisting of one or more chemotherapeutic agents, an anti-inflammatory agent, cytolytic agent, a pharmaceutically acceptable carrier, and a combination thereof.

22. The method according to claim 18, further comprising administering to the individual a pharmaceutically effective amount of one or more chemotherapeutic agents.

23. The method according to claim 18, further comprising administering to the individual a pharmaceutically effective amount of an anti-inflammatory agent.

24. A method of treating an individual bearing a solid nonlymphoid tumor, the method comprising administering to the individual a composition, wherein the composition comprises an affinity ligand which selectively binds to a B cell determinant, wherein the B cells targeted in the method and by the composition are nonmalignant B cells, and wherein the composition is administered in an amount effective to reduce the incidence of metastasis.

25. The method according to claim 24, wherein the nonmalignant B cells are B cells selected from the group consisting of mature B cells, memory B cells, CD19+ sTn+ B cells, CD19+ CD21+ B cells, CD19+CD21+ sTn+ B cells, CD19+ CD5+ B cells, CD19+ CD5+ sTn+ B cells, and a combination thereof.

26. The method according to claim 24, wherein the composition is a chimeric anti-CD20 monoclonal antibody.

27. The method according to claim 24, wherein the composition is administered by a mode selected from the group consisting of parenterally, and in a site directed method in which the composition is delivered to a localized region or a tissue selected from the group consisting of lymphoid tissue, solid nonlymphoid tumor, an organ containing the solid, non-lymphoid tumor, and a combination thereof.

28. The method according to claim 24, wherein the composition further comprises an additional component selected from the group consisting of one or more chemotherapeutic agents, an anti-inflammatory agent, cytolytic agent, a pharmaceutically acceptable carrier, and a combination thereof.

29. The method according to claim 24, further comprising administering to the individual a pharmaceutically effective amount of one or more chemotherapeutic agents.

30. The method according to claim 24, further comprising administering to the individual a pharmaceutically effective amount of an anti-inflammatory agent.

31. A site-directed method of treating an individual bearing a solid nonlymphoid tumor, the method comprising: administering to the individual a composition, wherein the composition comprises an affinity ligand which selectively binds to a B cell determinant, wherein the B cells targeted in the method and by the composition are nonmalignant B cells, wherein the composition is administered into a vessel that accesses a tissue, wherein the tissue comprises a tissue selected from the group consisting of lymphoid tissue, solid, nonlymphoid tumor, and a combination thereof, and wherein the composition is administered in an amount effective to reduce the incidence of metastasis.

32. The method according to claim 31, wherein the tissue is selected from the group consisting of lymphoid tissue, and a combination of lymphoid tissue solid, nonlymphoid tumor; and wherein the lymphoid tissue is selected from the group consisting of lymphoid tissue regional to solid, nonlymphoid tumor, lymphoid tissue distal to solid, nonlymphoid tumor, and a combination thereof.

33. The method according to claim 31, wherein the nonmalignant B cells are B cells selected from the group consisting of mature B cells, memory B cells, CD19+ sTn+ B cells, CD19+ CD21+ B cells, CD19+CD21+ sTn+ B cells, CD19+ CD5+ B cells, CD19+ CD5+ sTn+ B cells, and a combination thereof.

34. The method according to claim 31, wherein the composition is a chimeric anti-CD20 monoclonal antibody.

35. The method according to claim 31, wherein the composition further comprises an additional component selected from the group consisting of one or more chemotherapeutic agents, an anti-inflammatory agent, cytolytic agent, a pharmaceutically acceptable carrier, and a combination thereof.

36. The method according to claim 31, further comprising administering to the individual a pharmaceutically effective amount of one or more chemotherapeutic agents.

37. The method according to claim 31, further comprising administering to the individual a pharmaceutically effective amount of an anti-inflammatory agent.

38. The method according to claim 31, wherein a catheter is used for site-directed delivery of the composition to tissues in a region selected from the group consisting of the abdomen, colon, and a combination thereof.

39. The method according to claim 38, further comprising administering to the individual a pharmaceutically effective amount of one or more chemotherapeutic agents.

40. The method according to claim 38, further comprising administering to the individual a pharmaceutically effective amount of an anti-inflammatory agent.

41. A method of treating an individual bearing a solid nonlymphoid tumor, the method comprising administering to the individual a composition, wherein the composition comprises an affinity ligand which selectively binds to a B cell determinant, wherein the B cells targeted in the method and by the composition are nonmalignant B cells, wherein the composition is administered intravenously, and wherein the composition is administered in an amount effective to reduce the incidence of metastasis.

42. The method according to claim 41, wherein the nonmalignant B cells are B cells selected from the group consisting of mature B cells, memory B cells, CD19+ sTn+ B cells, CD19+ CD21+ B cells, CD19+CD21+ sTn+ B cells, CD19+CD5+ B cells, CD19+ CD5+ sTn+ B cells, and a combination thereof.

43. The method according to claim 41, wherein the composition is a chimeric anti-CD20 monoclonal antibody.

44. The method according to claim 41, wherein the composition further comprises an additional component selected from the group consisting of one or more chemotherapeutic agents, an anti-inflammatory agent, cytolytic agent, a pharmaceutically acceptable carrier, and a combination thereof.

45. The method according to claim 41, further comprising administering to the individual a pharmaceutically effective amount of one or more chemotherapeutic agents.

46. The method according to claim 41, further comprising administering to the individual a pharmaceutically effective amount of an anti-inflammatory agent.

* * * * *